US006501983B1

(12) United States Patent
Natarajan et al.

(10) Patent No.: US 6,501,983 B1
(45) Date of Patent: Dec. 31, 2002

(54) IMPLANTABLE MYOCARDIAL ISCHEMIA DETECTION, INDICATION AND ACTION TECHNOLOGY

(75) Inventors: Ananth Natarajan, New Port Richey, FL (US); Nitish V. Thakor, Clarksville, MD (US)

(73) Assignee: Infinite Biomedical Technologies, LLC, Baltimore, MD (US)

( * ) Notice: Subject to any disclaimer, the term of this patent is extended or adjusted under 35 U.S.C. 154(b) by 0 days.

(21) Appl. No.: 09/369,576

(22) Filed: Aug. 6, 1999

Related U.S. Application Data
(60) Provisional application No. 60/095,635, filed on Aug. 7, 1998.

(51) Int. Cl.[7] .............................. A61B 5/04; A61B 5/02
(52) U.S. Cl. ....................... 600/517; 600/509; 600/515; 600/508
(58) Field of Search ................................. 600/481, 483, 600/485, 486, 488, 508, 509, 510, 511, 512, 513, 514, 515, 516, 517, 518, 519, 520, 521, 522, 523, 524, 525, 526, 527

(56) References Cited

U.S. PATENT DOCUMENTS

| 4,172,451 | A | 10/1979 | Kline |
| 4,595,012 | A | 6/1986 | Webler et al. |
| 4,681,117 | A | 7/1987 | Brodman et al. |
| 4,727,877 | A | 3/1988 | Kallok |
| 4,830,006 | A | 5/1989 | Haluska et al. |
| 4,924,875 | A | 5/1990 | Chamoun |
| 4,932,407 | A | 6/1990 | Williams |
| 4,974,162 | A | 11/1990 | Siegel et al. |
| 5,003,976 | A | 4/1991 | Alt |
| 5,010,888 | A | 4/1991 | Jadvar et al. |
| 5,014,696 | A | 5/1991 | Mehra |
| 5,105,826 | A | 4/1992 | Smits et al. |
| 5,111,816 | A | 5/1992 | Pless et al. |
| 5,113,869 | A | * 5/1992 | Nappholz et al. ........... 600/508 |
| 5,135,004 | A | 8/1992 | Adams et al. |
| 5,158,079 | A | * 10/1992 | Adams et al. ............... 600/517 |
| 5,159,932 | A | 11/1992 | Zanetti et al. |
| 5,199,428 | A | 4/1993 | Obel et al. |
| 5,203,348 | A | 4/1993 | Dahl et al. |
| 5,313,953 | A | 5/1994 | Yomtov et al. |
| 5,365,426 | A | 11/1994 | Siegel et al. |
| 5,388,578 | A | 2/1995 | Yomtov et al. |
| 5,403,351 | A | 4/1995 | Saksena |
| 5,411,031 | A | * 5/1995 | Yomtov ....................... 600/519 |
| 5,417,717 | A | 5/1995 | Salo et al. |
| 5,431,681 | A | 7/1995 | Helland |
| 5,433,198 | A | 7/1995 | Desai |

(List continued on next page.)

OTHER PUBLICATIONS

Boris Gramatikov, Sun Yi–Chun, Herve Rix, Pere Caminal, and Nitish V. Thakor, "Multiresolution Wavelet Analysis of the Body Surface ECG Before and After Angioplasty," *Annals of Biomedical Engineering*, vol. 23, pp. 553–561 (1995).

Boris Gramatikov and Nitish Thakor, "Wavelet Analysis of Coronary Occlusion Related Changes in ECG" IEEE 0–7803–1377–1/93 (1993).

Primary Examiner—Kevin Shaver
Assistant Examiner—Navin Natnithithadha
(74) Attorney, Agent, or Firm—Konrad Raynes Victor & Mann LLP; Alan S. Raynes

(57) ABSTRACT

One embodiment enables detection of MI/I and emerging infarction in an implantable system. A plurality of devices may be used to gather and interpret data from within the heart, from the heart surface, and/or from the thoracic cavity. The apparatus may further alert the patient and/or communicate the condition to an external device or medical caregiver. Additionally, the implanted apparatus may initiate therapy of MI/I and emerging infarction.

122 Claims, 13 Drawing Sheets

U.S. PATENT DOCUMENTS

| | | |
|---|---|---|
| 5,482,037 A | 1/1996 | Borghi |
| 5,515,859 A | 5/1996 | Paz |
| 5,527,344 A | 6/1996 | Arzbaecher et al. |
| 5,531,768 A | 7/1996 | Alferness et al. |
| 5,545,183 A | 8/1996 | Altman |
| 6,016,443 A * | 1/2000 | Ekwall et al. .............. 600/519 |
| 6,112,116 A * | 8/2000 | Fischell et al. ............. 600/517 |
| 6,115,628 A * | 9/2000 | Stadler et al. .............. 600/517 |
| 6,115,630 A * | 9/2000 | Stadler et al. .............. 600/521 |
| 6,128,526 A * | 10/2000 | Stadler et al. .............. 600/517 |

* cited by examiner

IMPLANTABLE MYOCARDIAL ISCHEMIA DETECTION, INDICATION AND ACTION TECHNOLOGY

This application claims the benefit of U.S. Provisional Application No. 60/095,635, filed Aug. 7, 1998, entitled "Method and Apparatus for In Vivo Detection of Myocardial Ischemia."

FIELD OF INVENTION

The present invention relates to methods and apparatus for detection and treatment of the disease process known as myocardial ischemia and/or infarction (MI/I).

BACKGROUND

Ischemia occurs when the blood supply to the heart muscle is temporarily or permanently reduced, such as may result from the occlusion of a coronary artery. This occlusion may lead to local ischemia or infarction of the heart muscle. Ischemia may also occur over large sections of the heart muscle due to conditions such as cardiac arrest, heart failure, or a variety of arrhythmias. The ischemic event can be of the so called "silent type" described in medical literature (e.g. not manifesting itself in terms of symptoms experience by the patient or obvious external indications). The event can also be chronic with continuously evolving symptoms and severity due to underlying heart disease, or very abrupt and possibly even fatal due to infarction of large enough area of the heart to cause a large myocardial infarction.

The ischemic event often causes the performance of the heart to be impaired and consequently manifests itself through changes in the electrical (e.g. the electrocardiogram signal), functional (e.g pressure, flow, etc.) or metabolic (e.g. blood or tissue oxygen, pH, etc.) parameters of the cardiac function.

The conventional approach to detection of MI/I is to analyze the electrocardiogram (ECG). An ischemic event results in changes in the electrophysiological properties of the heart muscle that eventually manifest themselves as changes in the ECG signal. The current state of the art is to record these ECG signals from the body surface using amplifiers and associated instrumentation. A standardized set of electrodes in an arrangement known as a 12-lead ECG has been developed. The conventional approach to the detection of ischemia and infarction relies on analysis and interpretation of characteristic features of the ECG signal such as the ST-segment, the T-wave or the Q-wave. Computer-based technology has been employed to monitor, display, and semi-automatically or automatically analyze the ischemic ECG changes described above. The present technology includes ECG machines used in doctor's office, portable ECG machines known has Holter recorders, bedside monitors with displays, and sophisticated computer-based system for automatic analysis of the ECG signals.

Technology exists for providing therapy once ischemia is detected. The most common approach involves thrombolytic therapy (by external infusion of drugs such as TPA or streptokinase) or opening of the blocked vessels using a variety of angioplasty catheter devices. In the event that ischemic condition results in malignant arrhythmia or arrest of the heart, an external defibrillator may be used to shock the heart and restore the cardiac rhythm.

Technology also exists for implanting therapeutic devices for treating electrical conduction disturbances or arrhythmias of the heart. These devices include implantable pacemakers, cardioverters and atrial and ventricular defibrillators, drug infusion pumps as well as cardiac assist devices. The implantable devices typically use intracavitary leads to sense the electrogram (EGM) and then provide electrical therapy (pacing or defibrillation) or mechanical therapy (pumping blood). These devices sense the EGM and then utilize the features, such as improper conduction (in case of a pacemaker) or a fatal rhythm (in case of a defibrillator), or simply timing (to coordinate mechanical pumping). Notably, these devices do not specialize in the task of detecting, alerting the patient or treating ischemic heart disease.

Ischemia detection and analyses are usually done manually by the expert cardiologist or by computers employing algorithms to detect ischemia-related changes in the ECG signals. The preferred features of the ischemia detecting computer algorithms are the ST-segment and the T-wave. These features show elevation, depression or inversion of these ECG signals associated with ischemia. The computer then carries out a careful measurement of the degree of elevation/depression in a specific lead. By identifying ischemia dependent changes from specific leads, the ischemic event is attributed to a specific region of the heart.

The current approach to diagnosis is that after an ischemic event is perceived by the patient, they contact medical personnel such as the "911" system or their personal physician. Within the clinical setting, the patient is often monitored using a short recording of the ECG signal which may be interpreted by a physician. Alternately, the high risk patient may be continuously monitored at the bedside in a cardiac intensive care unit. Therapy may include using drugs such as TPA, use of catheters for angioplasty (opening the blocked coronary vessel using a balloon or laser), or providing life support back up such as defibrillation.

The aforementioned cardiovascular medical monitoring technology and medical practice have several significant drawbacks in regard to the detection and treatment of coronary ischemia which can result in severe consequences to the patient up to and including death. They include the following:

1) Not being able to immediately alert the patient and/or the physician of an ischemic event, particularly a life threatening event.
2) Not being ambulatory with the patient; and/or an inability to provide continuous monitoring to the patient and indication of the necessary diagnostic information to the physician.
3) Requiring input and interpretation of a physician or medical practitioner when one may not be present.
4) Requiring monitoring devices external to the body, such as an ECG monitor or external defibrillator, which are usually only available in medical centers and hospitals, and which further need special expertise and attention from medical personnel.
5) Reduced sensitivity or otherwise inability to detect ischemic events due to loss of sensitivity from use of external electrodes.
6) Loss of specificity as to the site of ischemia due to inadequate placement of electrodes in the vicinity of the ischemia or infarction.
7) Needing sophisticated expertise of a cardiologist to interpret the clinical condition or needing monitoring instruments with sophisticated computer-aided ECG signal analysis capabilities.
8) Over reliance on use of ECG signals for detection and inability to utilize and integrate other physiological data, (e,g pressure, blood flow, and PO2).

9) Inability to immediately alert the patient or the physician of the impending or emerging ischemic condition.

10) Inability to provide immediate treatment, particularly for life-threatening events (e.g. myocardial infarction, cardiac arrest).

SUMMARY OF THE INVENTION

Certain embodiments of the present invention relate to methods and devices for detection of myocardial ischemia and/or infarction (MI/I). Preferred embodiments relate to electrodes and sensors, devices and methods for interpreting ischemic conditions, devices and methods for initiating the procedure to alert the patient and/or the care-giver, and devices and methods for connecting with a device that provides therapy. MI/I may be detected using implantable devices and methods according to certain embodiments of the present invention.

Embodiments may include a stand alone device or a modification of another implantable device such as a pacemaker, cardioverter, defibrillator, drug delivery pump or an assist device. Embodiments may use a variety of in vivo sensors located inside the human torso and/or inside the heart. The sensor device preferably includes electrodes that are indwelling in the heart, on or in the vicinity of the heart, under the skin, under the musculature, implanted in the thoracic or abdominal cavity. Preferably the sensor device also includes strategic placement of the electrodes to capture the EGM signal from various positions and orientations with respect to the heart. The sensor device also preferably includes other hemodynamic or mechanical sensors that are sensitive to the condition of the heart in MI/I. MI/I may be recognized using analysis of the features of the signal, namely the EGM, recorded by the electrodes and sensors. The features of the EGM signal (namely, depolarization and repolarization), morphology, and analytical information such as the spectrum, wavelet transform, time-frequency distribution and others, are utilized in the interpretation and recognition of the MI/I condition. Separately or in conjunction, the hemodynamic (namely, blood pO2, pH, conductance, etc.) and mechanical parameters (blood pressure, blood flow, etc.) are sensed according to the embodiments of this invention. MI/I is then recognized by integrating some or all of the sensor information. Embodiments may detect this MI/I event and alert the patient using a variety of methods, including but not limited to vibration, electrical stimulation, auditory feedback, and telemetry. The device to alert the patient may in certain embodiments be incorporated within the instrument itself. The patient may be alerted by direct communication via electrical, sound, vibration or other means or indirect communication to an external device in an electromagnetic link with the implanted device. Once the MI/I event is identified, the device may also institute therapy, such as infusion of a thrombolytic agent or delivering life saving shock in case of an arrest, semi-automatically or automatically. The therapy giving device may be integrated with the MI/I detection, MI/I analysis, and/or patient alerting device into an integrated or separate stand alone system.

Embodiments of the invention may be used to detect MI/I from inside the body as compared with the traditional approach of detection by placing electrodes on the outer body surface of the torso. This is made feasible in certain embodiments by using the MI/I detection technology in an implantable device. Embodiments utilize sensors, such as electrodes and leads, that record the EGM signal from inside the chest in the vicinity of the heart and/or from electrodes placed on the heart, and/or using catheters or leads placed inside the cavities (atria and ventricles). Embodiments may include built-in interfaces to electrodes, namely circuits for amplification and filtering of the signals, and the circuit for digitization (analog-to-digital conversion) and processing (microprocessor). Embodiments of the implantable device, using its microprocessor, analyze the features of the EGM signal from these leads to detect an ischemic event.

Embodiments also relate to the design, construction and placement of electrode sensors. Embodiments may include an electrode lead with multiple sensors capable of recording EGM from multiple, strategic locations in the chest or in and around the heart. This embodiment also includes utilization of the body of the instrument and single or multiple leads.

Embodiments also relate to detection of the ischemic event including identifying particular features of the EGM signal. These features include depolarization (i.e. initial excitation of the heart when a beat is initiated, coincident with the body surface QRS complex) and repolarization (i.e. the subsequent repolarization of the heart coincident with the body surface ST-segment and T-wave). MI/I results in alteration in depolarization and repolarization waves in selected regions of the heart, for the case of focal ischemia, or the entire heart, for the case of global ischemia. These changes alter the action potential (of heart cells) as well as the conduction pattern (in selected regions or the whole heart). The alterations in action potential shape and conduction change together alter both the depolarization features as well as the repolarization features). Depending on where an electrode is placed, these features may be seen in different recordings. The electrodes pick up the local signal (from the heart muscle in its vicinity) as well as the distal signal (distal muscle areas as well as the whole heart). The characteristics of this signal are identified in the form of shape changes, and these shape changes can be identified in a variety of ways, including temporal, spectral, and combined approaches.

The MI/I detection technology according to embodiments of the present invention, may also utilize non-electrical measures, including hemodynamic and mechanical parameters. An MI/I event may result in a degree of deprivation of oxygen to the heart muscle. This in turn may result in a decreased ability to perfuse the heart muscle as well as the body. This may result in a cyclical reduction in the mechanical performance in terms of contractility and pumping action of the heart. Sensors placed inside the blood stream pick up the changes in blood oxygen, pH, conductance, etc. resulting from the MI/I event. The MI/I event would lead to small changes in case of mild ischemia or infarct or significant changes in case of global ischemia or cardiac arrest. The sensors are usually placed inside a catheter or a lead, although some times in the body of the instrument, and then measurements may be made via the electronic circuit interfaces inside the implantable device. The mechanical function of the heart may be detected utilizing sensors and leads, including those for pressure, volume, movement, contractility, and flow.

Embodiments also relate to methods and devices for signaling the host patient or others (such as medical personnel) to the incidence of MI/I. When MI/I is detected, it is imperative to take therapeutic actions rapidly and even immediately. Thus, the patient needs to be informed and the caregiver physician needs to be informed. Embodiments of the invention include devices and methods for communication between the implantable device and the host/physician. One of these approaches is to use radio-frequency or radiotelemetry, while another is to communicate through electrical stimulation. Other approaches, including sound, and magnetic fields are also devised. Embodiments may also utilize long distance, remote and wireless means of communication using telephone, telemetry, Internet and other communication schemes. Embodiments may also include the code of communication by which the information pertinent to MI/I is presented in detail. This code may be either analog or digital, relayed via the communication link, and then decoded by the receiving instrument or individual. The code primarily signals to the host patient, or the external device attached to the patient, or directly to the medical caregiver, the condition of MI/I. The code may include information about EGM, the MI/I condition, and other related diagnostic information. The code may also include recommendation and instructions to provide an immediate therapy to the patient to treat MI/I.

Another aspect of certain embodiments of the invention includes coupling of the MI/I detection technology to a variety of therapeutic devices. The implantable MI/I detection technology makes it feasible to rapidly initiate therapy through direct access to the body, circulatory system or the heart. In some circumstances it is desirable to infuse drug such as Streptokinase or TPA to treat the patient. Other drugs may also be infused immediately or subsequently on a steady state basis. In other instances it is desirable to carry out procedures such as angioplasty. In case the MI/I event leads to a life-threatening arrhythmia or cardiac arrest, means to treat the arrhythmias to resuscitate the heart are disclosed. These may include use of electrical pacing, cardioversion and/or defibrillation. In case the MI/I event leads to a failure of the heart, means to assist the heart are disclosed. These assistive devices include left or right ventricular assistive device and artificial heart pump. Embodiments may declare interface of the implantable myocardial ischemia detection technology to these therapeutic approaches and the use of these therapies upon discovery of MI/I by the implanted devices.

Another aspect of certain embodiments of the invention includes the use of the technology in an implantable device. The implantable device may include a hermetically sealed can, electronics, analog and digital logic, microprocessor, power source, leads and sensors, circuits and devices to alert the patient, communication link and interface to the external diagnostic and therapeutic means. Embodiments also include modification of implantable arrhythmia detection devices, pacemakers, defibrillators, infusion pumps, or assist devices to have the novel features described above. The technology used in embodiments of the present invention can be partially or fully integrated into these instruments. Embodiments further include hardware, software or firmware modification of the aforementioned devices to have MI/I detection, alerting and therapy initiating features.

BRIEF DESCRIPTION OF THE DRAWINGS

Certain embodiments of the invention are described with reference to the accompanying drawings which, for illustrative purposes, are not necessarily drawn to scale.

FIG. 8(*b*) illustrates the implantable MI/I detection technology piggy-backed or incorporated as a part of a modified implantable pacemaker or a cardioverter-defibrillator according to embodiments of the present invention.

DETAILED DESCRIPTION

Certain embodiments of the invention pertain to methods and devices for detecting ischemia or infarction, diagnosing, alerting the patient and/or treating the ischemic heart disease.

Figure 1:
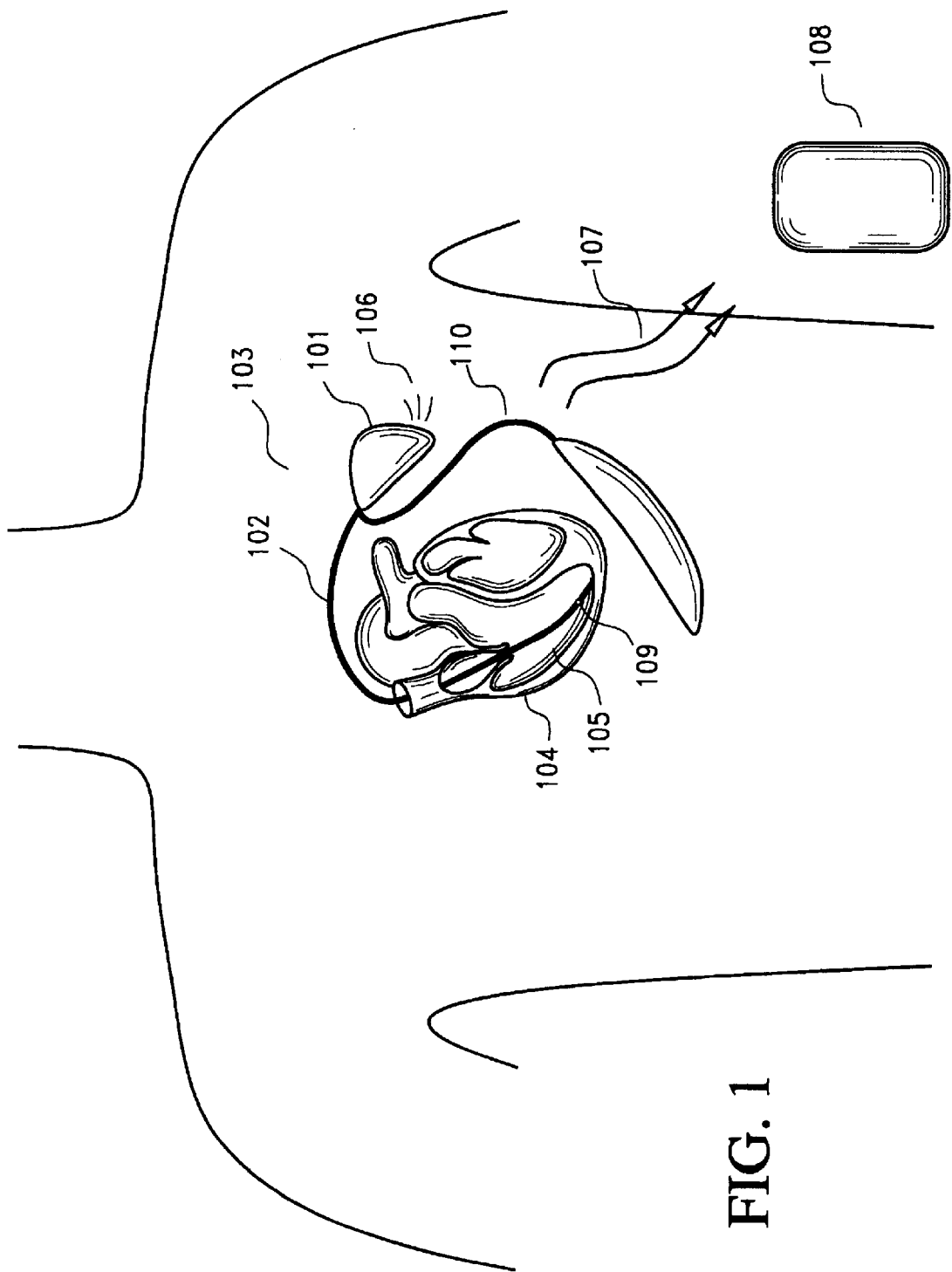
FIG. 1 illustrates a schematic illustration of the torso and heart which also includes the implantable device, its sensing lead, an alarm means, a therapy device, and a communication means to an external device according to an embodiment of the present invention.

Implantable myocardial ischemia and/or infarction (MI/I) detection technology according to certain preferred embodiments is illustrated in FIG. 1. Embodiments include methods and devices to detect and treat MI/I. One embodiment of a method includes: i) placement/implantation of the device inside the chest or other body cavity, ii) placement and implantation of electrodes and sensors to selected areas of the myocardium, iii) connection of one or more of the electrodes and sensors to the implanted device, iv) detection of an ischemic event by the analysis of the EGM signal and sensor data, v) the method of analysis of the EGM signal using signal processing means in time and frequency domain, vi) communicating the stored EGM signals to an external device using telecommunication means, vii) alerting the patient of the event, vi) communication with the medical attendant using telecommunication means, and vii) initiating or implementing medical therapy for MI/I. Embodiments may include some or all of the above elements, which are described in more detail below.

One preferred embodiment is illustrated in FIG. 1. It includes a plurality of devices (101) and sensors (102) that are implanted in the human body (103). Referring to FIG. 1, this implementation may include one or more of the following steps: i) a device that would reside inside the body (103) and alert the patient (106) or the medical attendant of an impending or ongoing ischemic event and undertake therapeutic action, ii) one or more implanted sensors (102) positioned in selected areas of the heart (104), such as a ventricular cavity (105), and connected to the aforementioned device, iii) detecting an ischemic event, iv) alerting the patient of the event as depicted in (106), v) communication, as depicted in (107) with a device external to the body (108) or a medical attendant, vi) administration of medical therapy via an intracavitary pacing electrode (109), infusion of drug through the body of the lead (102) or shocking the heart between leads (102 and 110).

Figure 2A:
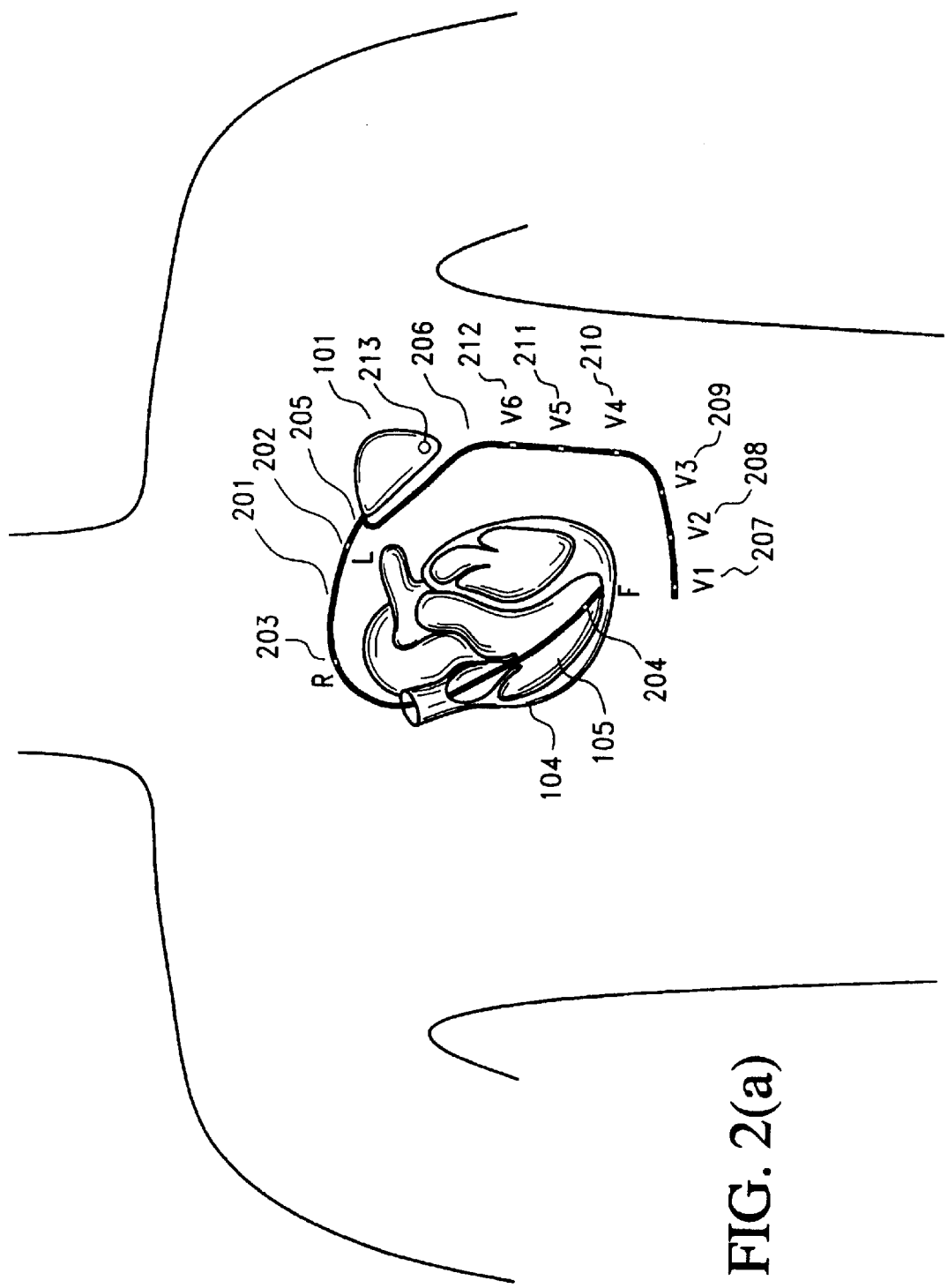
FIG. 2(*a*) illustrates a preferred embodiment including an implanted device such as a pacemaker with a full 12-lead electrocardiographic configuration (L, R, F and V1 through V6, and ground reference) using an implantable intracavitary and intrathoracic lead; (b) illustrates a second preferred embodiment using an implanted device and a single suitably positioned intrathoracic lead with multiple sensors in the chest and the ventricular cavity of the heart; and (c) illustrates a third preferred embodiment with a suitably placed device with multiple electrical contact sensors on the implanted device can and a suitably threaded lead through the thoracic, abdominal and the ventricular cavity along with the sensor means.

Another preferred embodiment of the device and its method of use is illustrated by FIG. 2(a). The device (101) is implanted in the thoracic cavity under the skin or muscle in the vicinity of the heart (104). The sensing may be accomplished by a detailed electrocardiographic system that provides a device for biopotential recording from locations around the heart that result in a more complete assessment of the ischemic regions of the heart. The leads are positioned in one or more configurations within the chest to form an internal Einthoven's triangle (an external Einthoven's triangle is a concept known in the art). This configuration provides the advantage of enhanced signal sensitivity for discrete selectable areas of the myocardium and allows for easy determination of particular cardiac vectors. The resultant 12-lead electrocardiographic system is employed by those skilled in the art on (not internal to) the chest to provide projection of the cardiac dipole at various electric field orientations. A cardiologist or a computer program is then employed to determine the site and degree of MI/I by interpretation of the electrocardiogram. In the present invention, an intra-thoracic lead system is designed to record the EGM activity using a plurality of sensors situated to record projections of the cardiac dipole from inside the body in a manner analogous to the Einthoven's triangle and a 12-lead recording system from outside the chest. A lead (201) system comprises a biocompatible insulated carrier device with a plurality of electrically conducting metallic sensors that conduct the EGM signal from in or around the chest to the circuitry within the implanted device. The lead depicted in FIG. 2 carries three sensors (202, 203, 204) corresponding respectively to the left arm (L), the right arm (R) and the foot (F) projections of the 12-lead system. A Wilson's central terminal, a central terminal derived through a resistive network, is provided to derive the leads I, II, III and the three augmented leads (external, but not internal, Wilson's central terminal and leads are concepts known to the art). The lead is attached to the body of the implanted, hermetically sealed device (101) via a connector (205) that provides a feed-through interface to the circuitry within. Another lead (206) carries additional sensors (207 through 212) corresponding respectively to the VI through V6 projections of the 12-lead electrocardiographic system. The body of the device or a conducting sensor incorporated there in provides the ground or the circuit common reference G (213). The sensor signals are electrically connected via the lead to the circuitry within the implanted device. The EGM signals recorded from this lead system is analyzed for the features of MI/I.

Figure 2B:
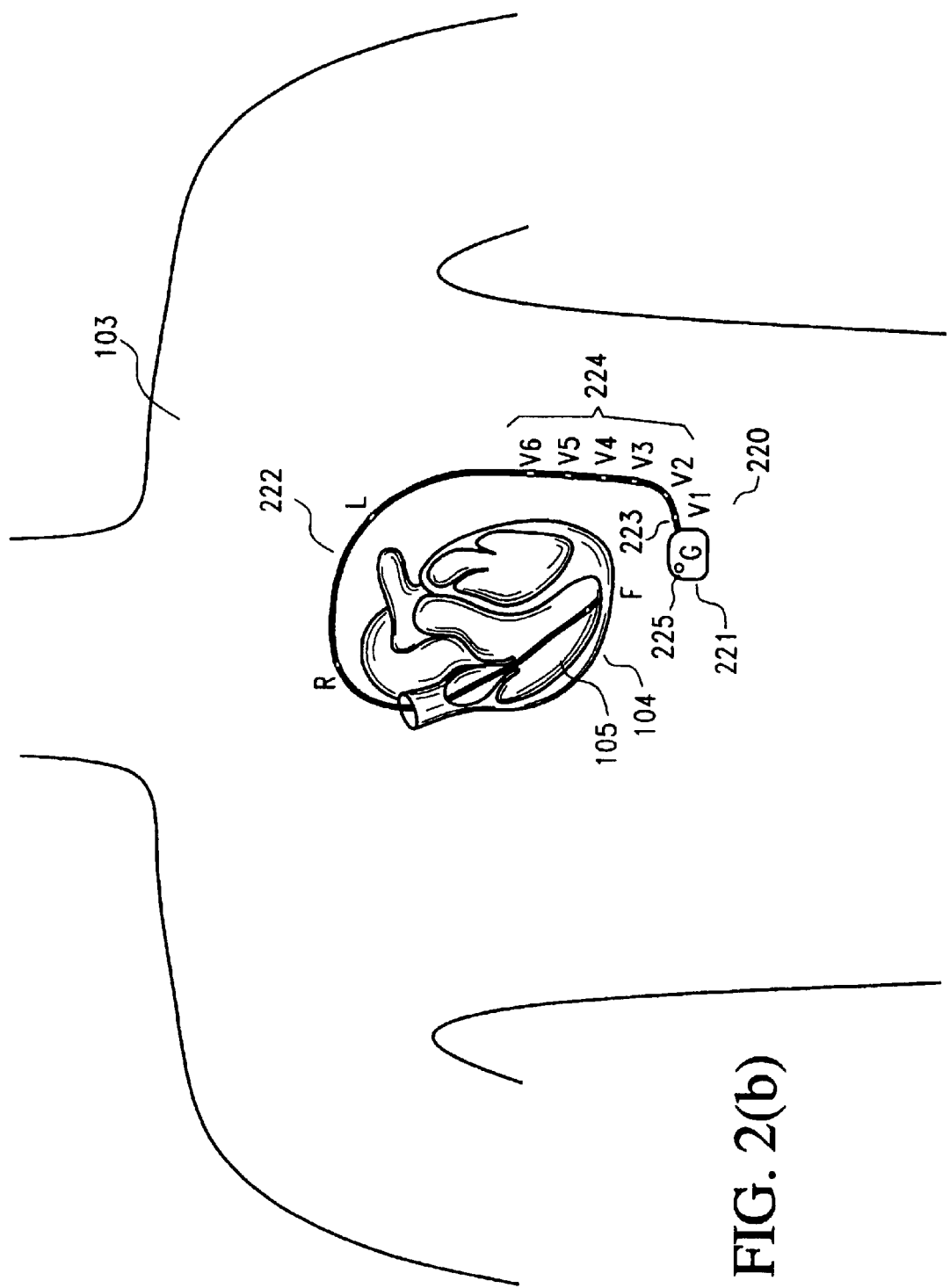

Another preferred embodiment shown in FIG. 2.2(b) comprises an implanted device (221) in the abdominal or lower thoracic cavity (220) with a preferred lead system (222) with a plurality of sensors. The lead system (222) makes a connection through a feed-through connector (223) to the circuitry of the implanted device (221). The lead (222) is suitably implanted within the thoracic cavity and in and around the heart (105) to place the sensors at locations that allow recordings analogous to the aforementioned 12-lead electrocardiographic system. The design involves the placement of the conducting sensors so that their placement inside the thoracic areas of the body (103) and in and around the heart (104,105) preferably corresponds to the 12-lead electrocardiographic system. Thus, the sensors V1 through V6 and L, R, and F (224) along with the ground reference G on the body of the device (225) represents all the electrodes needed to reconstruct the full electrocardiographic system, comprising leads I, II, III, augmented leads, and chest leads, suitable for implantable technology. The EGM signals from this lead system (222) may then be analyzed for the indications of MI/I.

Figure 2C:
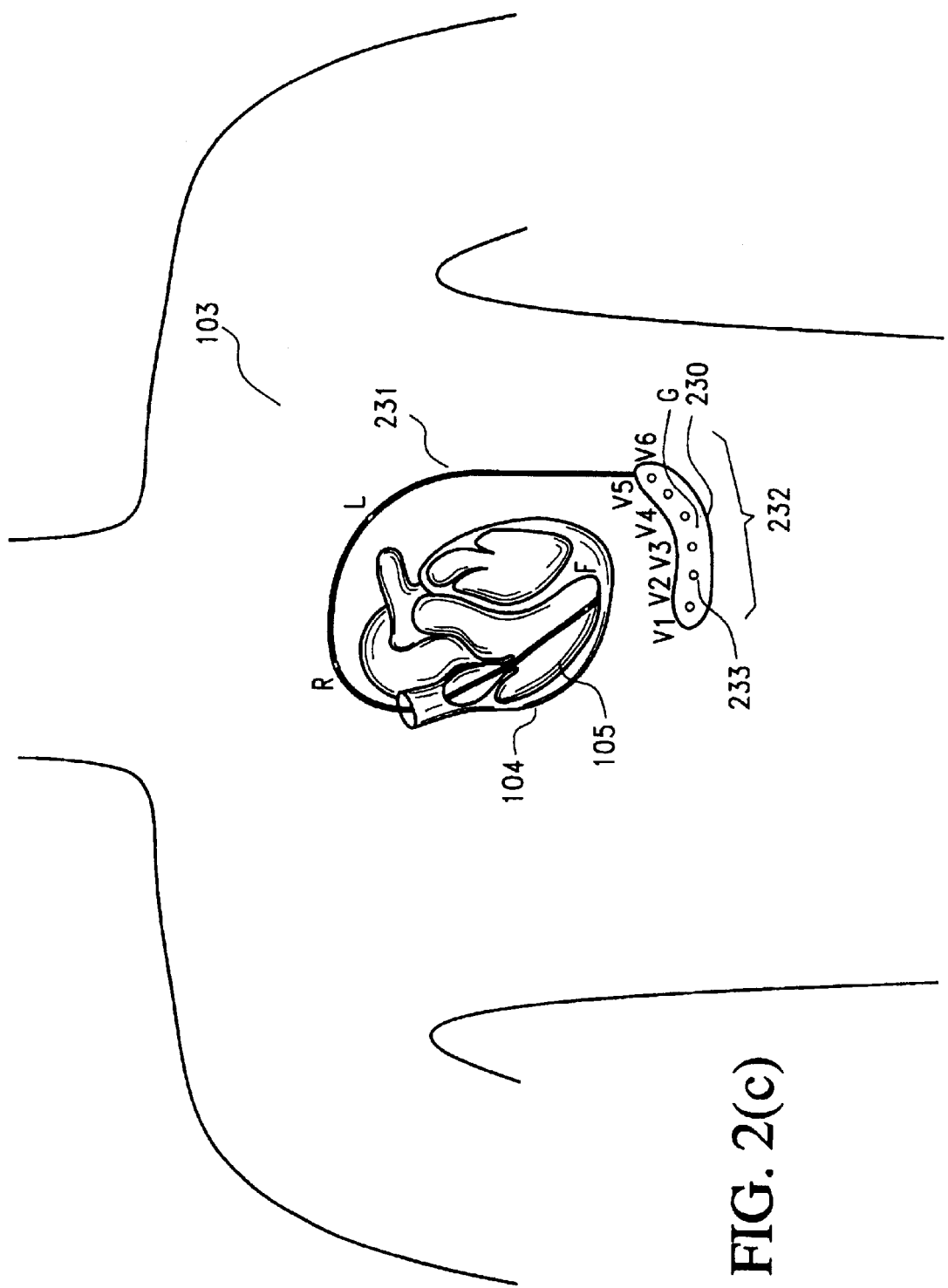

Another embodiment is depicted in FIG. 2(c). An implanted device (230) is located in the lower thoracic or abdominal cavity and a lead (231) with sensors therein is threaded through the intra-thoracic areas of the body (103) and in and around the heart (104,105). The lead carries the sensors L, R and F, while the body of the implanted device carries the sensors V1 through V6, wherein the sensor array shown as (232). The body of the device (230) carries the ground or the circuit common G, while the conductive sensor elements shown as the open circles are insulated from the body of the device as shown by the dark rings around the circular sensor body (233). This lead system suitably captures the EGM signals from the various regions of the body which are then electrically conducted by the lead (231) to the implanted device (230).

Figure 3:
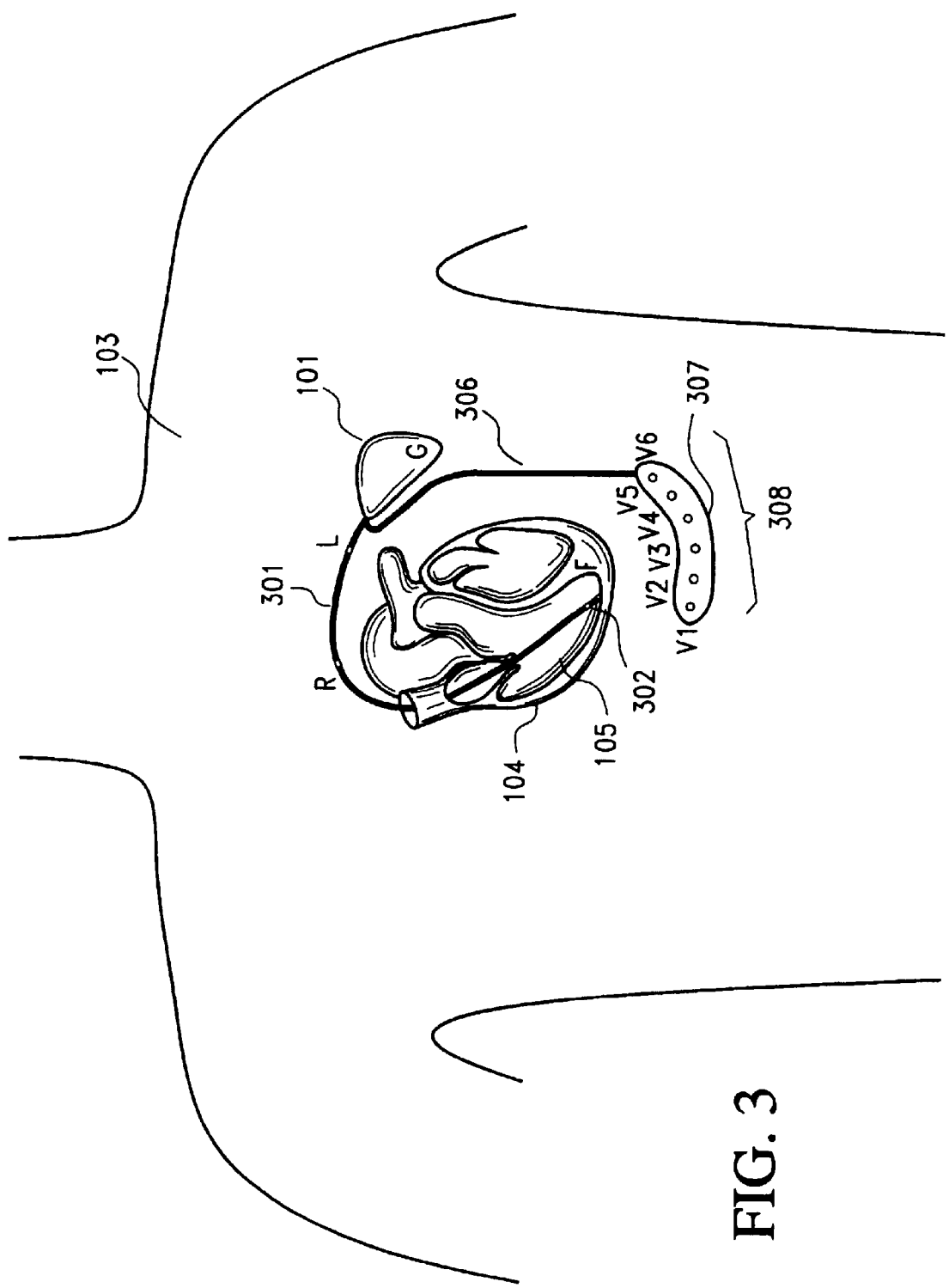
FIG. 3 illustrates a preferred embodiment, such as a cardioverter-defibrillator with suitable sensing or shocking lead with sensor means indwelling the heart and ventricular cavity and a series of sensors on the shocking lead on the epicardium or the thoracic, abdominal and ventricular cavity.

Still another embodiment is illustrated in FIG. 3. An implanted device (101) placed inside the body (103), utilizes a plurality of leads (301) and (306) and sensors therein. The lead (301) carries with it the sensors L, R and F for EGM sensing within and around the heart (104, 105). The lead 301 also carries plurality of sensors (302) for mechanical or hemodynamic information from within the ventricular cavity (105). The lead (306) connects sensor element (307) carrying plurality of sensor V1 through V6 (308). The body of the device (101) carries the ground reference G.

Figure 4:
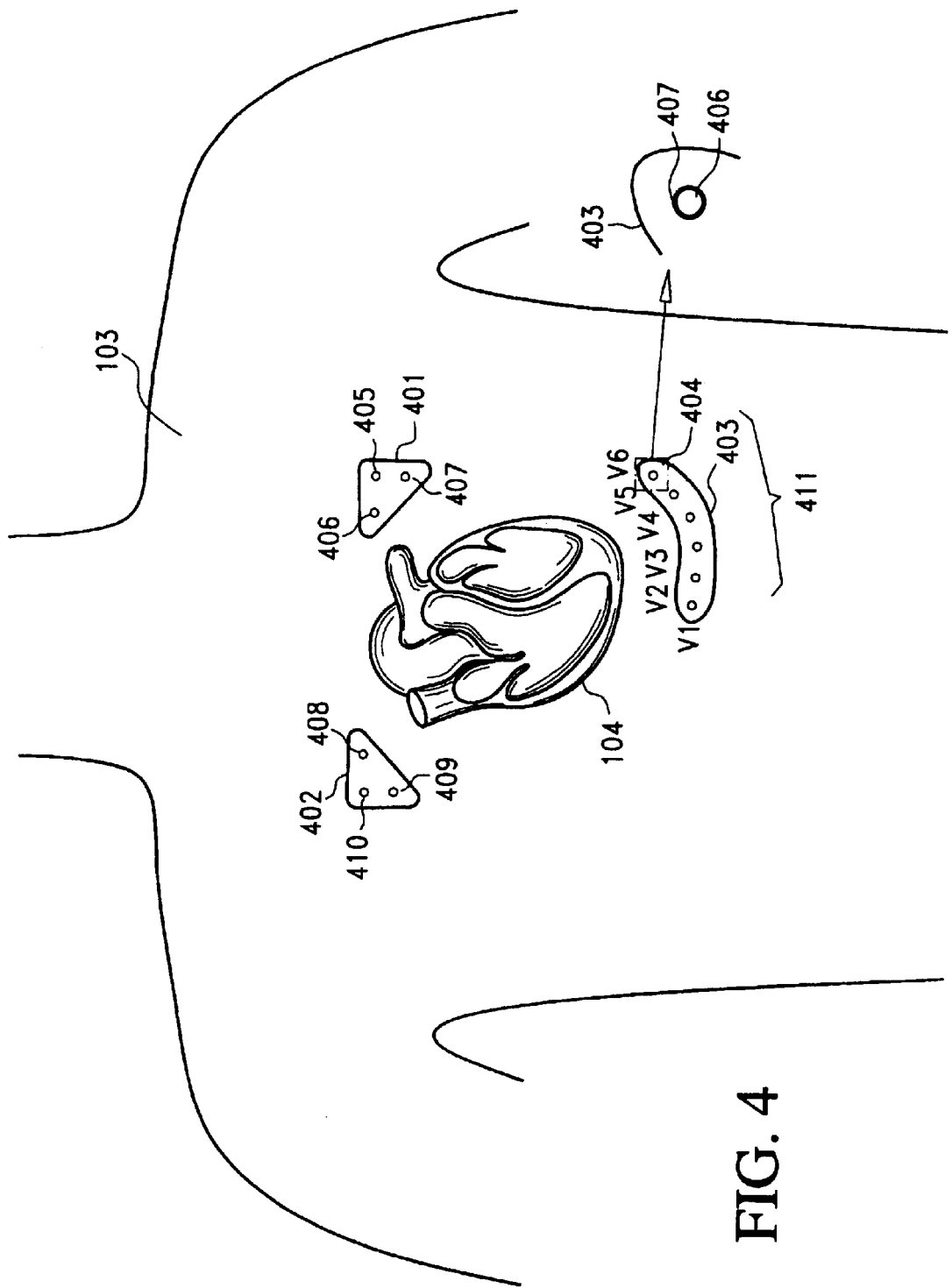
FIG. 4 illustrates three of the many placements and shapes of the implanted device inside the thoracic or abdominal cavity, and the sensor means on each can of the implanted device with each sensor insulated from the can (see the inset), according to embodiments of the present invention.

In yet another embodiment of the present invention, an implanted device is placed inside the chest in the proximity to the heart. The device is shaped in a manner so that it can carry on its case one or more leads (electrodes and their combination) suitable for recording multiple EGM signals. There are several locations that are preferred. FIG. 4 shows the thoracic part of the body (103), the heart (104), and three of the suggested locations and shapes of the device (401, 402, 403), each one of these locations and electrode placements is to be used independently and exclusively. These locations allow preferred orientation of the electrodes and leads for detection of EGM signal. For example, location (401) with three electrodes (405, 406, 407) give preferred orientation of the ECG in conventional left arm and lead I between (405, 406) signal from the cardiac dipole. The three sensors also give other projections from the heart when taken in pairs (406, 407) and (405, 407). The body of the can or an additional metal sensor insulated from the can is used as a ground reference. Alternately, the signals from the sensors (405, 406, 407) may be summed using resistive network, known, in external devices but not implanted devices, as Wilson's central terminal, to provide a common or reference signal. The location (403) analogously has 3 electrodes (408, 409, 410) which give the conventional right arm and lead I between (408, 409) signal, and other differential pairs II and III between (409, 410) and (408, 410). The location (403) has sensors V1 through V6 (411) giving 6 chest lead signals. In all these designs and placements the sensors are mounted on the encasement of the device known as the can and hence do not require separate leads or wires going out from the can via the feed-through to the heart or to the body. The can and the associated sensors can be entirely hermetically sealed and contained in a single case. The can may be made of a biocompatible material including, but not limited to stainless steel, titanium or a biocompatible engineered polymer such as polysulfone or polycarbonate and the like. The inset in FIG. 4 shows the electrical sensor element (406) surrounded by insulating ring (407) mounted on the can (403). The conducting sensor element provides electrical connection to the circuitry inside the can of the implanted device. The electrical sensor or the body of the implanted device serves as the ground or the circuit common reference. While three preferred embodiments are illustrated, the exact location of the implanted device and the electrical sensor elements can be varied to provide sensing and the lead oriented to improve the sensitivity to detection of the MI/I from a particular region of the heart. For example, a can at location (401) would pick up left and superior infarcts, a can at location (402) would pick up right and superior infarct, and a can at location (403) would pick up left or right inferior infarcts. In addition, in certain embodiments the container or can may be eliminated or integrated into one of the other components.

Figure 5A:
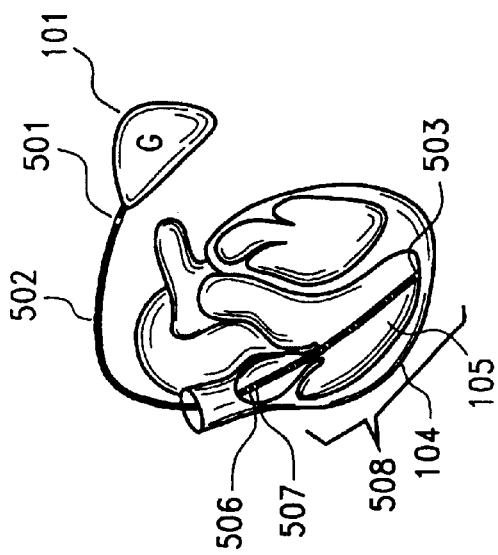
FIG. 5 illustrates three preferred embodiments with suitable implanted device in the thoracic cavity, placement of different electrode leads and sensors and their different configurations with respect to the heart. The sensor configuration includes leads with (a) unipolar, (b) bipolar sensing and (c) physiologic sensor means inside the ventricular cavity of the heart.
Figure 5B:
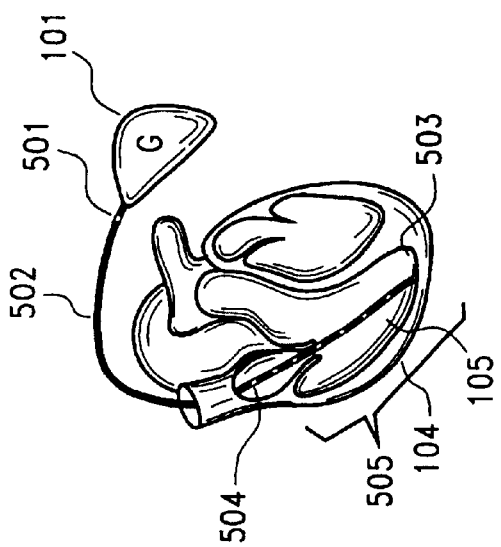
Figure 5C:
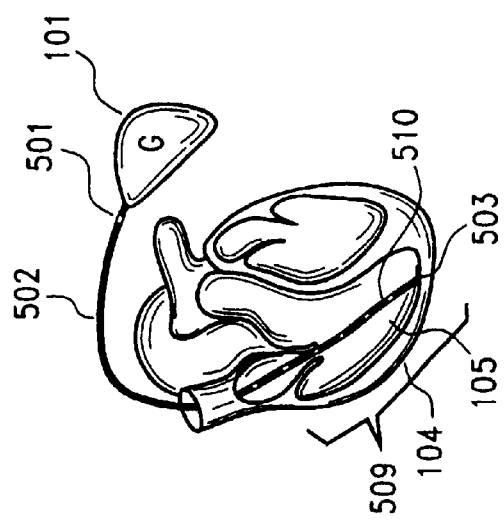

In a preferred embodiment of the device, an intracavitary indwelling lead system, as depicted in FIG. 5, is used to sense the EGM signals. Referring to FIG. 5(*a*), the implanted device (101) encases in the can the electronics while the body of the can serves as the ground or the reference G or otherwise a sensor on the lead serves as the ground or the reference (501). The intracavitary lead consists of a lead (502) going from the device (101) into the right ventricular cavity via the venous blood vessel by the methods well known in the art. The lead (502) may be preferentially threaded through the right or the left subclavian veins. The lead (502) may also be threaded through inferior vena cava or IVC. The lead (502) is placed in the atrial or the ventricular cavity or both. The lead (502) also may lodge in the SVC and through the septal region in the left ventricular cavity. The lead (502) may be placed in the left ventricle via the arterial vessel. The lead made of biocompatible material including, but not limited to polyurethane or silicon carries within it the metallic coil or wire for proper insertion of the lead (502). The lead (502) carries at its tip the pacing electrode (503) by which electrical stimulation is delivered to the heart muscle. Although depicted in this figure as being in contact with the ventricular muscle, the pacing electrode (503) may also be in contacting with atrial muscle or other suitable pacing regions on the heart surface. The sensing and the pacing electrodes may be designed into a single lead body or separate lead bodies. The atrial and ventricular chambers of the heart may be sensed and paced separately or jointly. The external body of the lead also carries the conducting sensor element such as (504) to contact and capture electrical signal from the cavity of the heart (105). A plurality of electrically conducting contact points (505) on the lead serve as sensor elements. As these sensor elements (504) span the atrium to the ventricle, typically on the right side of the heart, these sensor elements (504) capture the EGM signal associated with that part of the heart. In the preferred embodiment in FIG. 5 (*a*), the sensor elements are arranged in the unipolar configuration wherein the sensor elements are well separated from one another, each capable of capturing electrical signal with respect to the ground reference G on the body of the can or electrode (501). In another preferred embodiment illustrated in FIG. 5(*b*), the sensor elements are arranged in a bipolar configuration wherein pairs of sensor elements (506, 507) are closely spaced. A plurality of sensor element pairs (508) are arranged in the region spanning the atrium, ventricle or both. In another preferred embodiment, illustrated in FIG. 5(*c*), the sensor element can be at or close the tip of the catheter (510) and may include one or more of many hemodynamic sensors (e.g. pressure, pO2, pH, temperature, conductivity, etc.) or mechanical sensors (strain gauge, accelerometer, etc.).

Figure 6A:
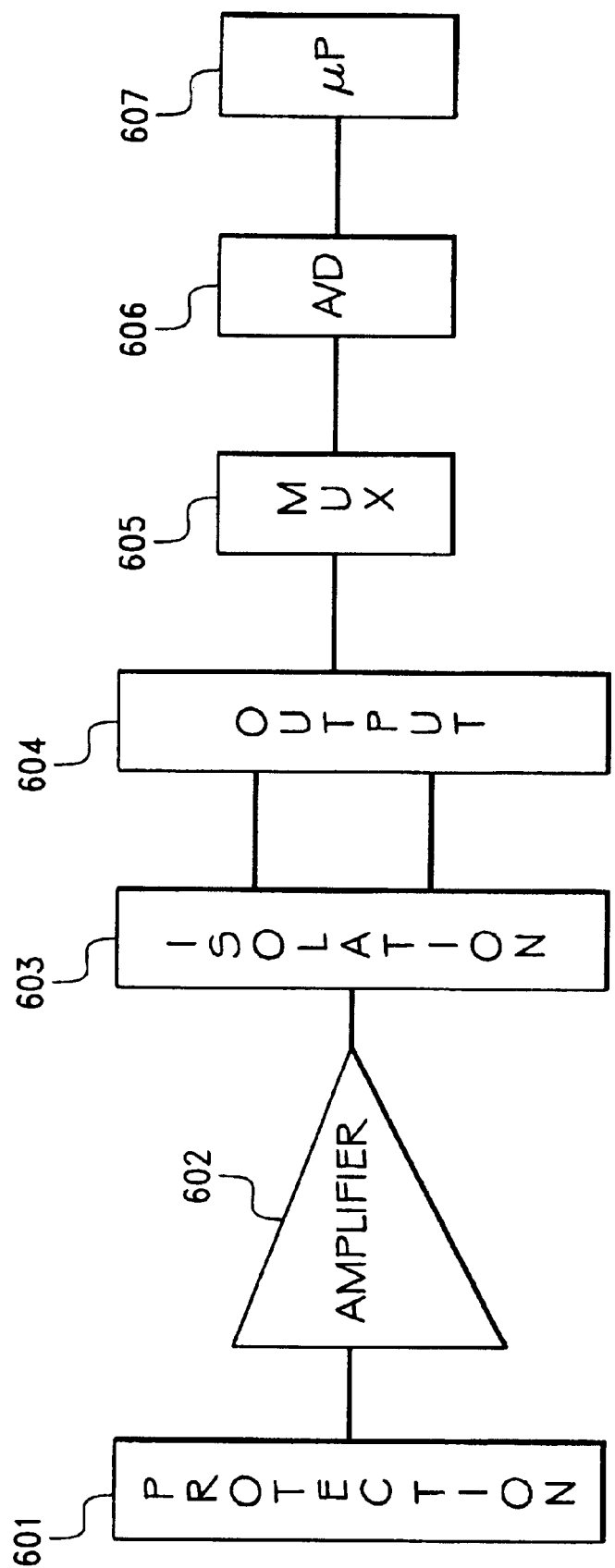
FIG. 6 illustrates the (a) electronics and microprocessor system used in the implantable myocardial ischemia detection device, and (b) the circuit diagram for amplification and filtering of the EGM signal, according to embodiments of the present invention.
Figure 6B:
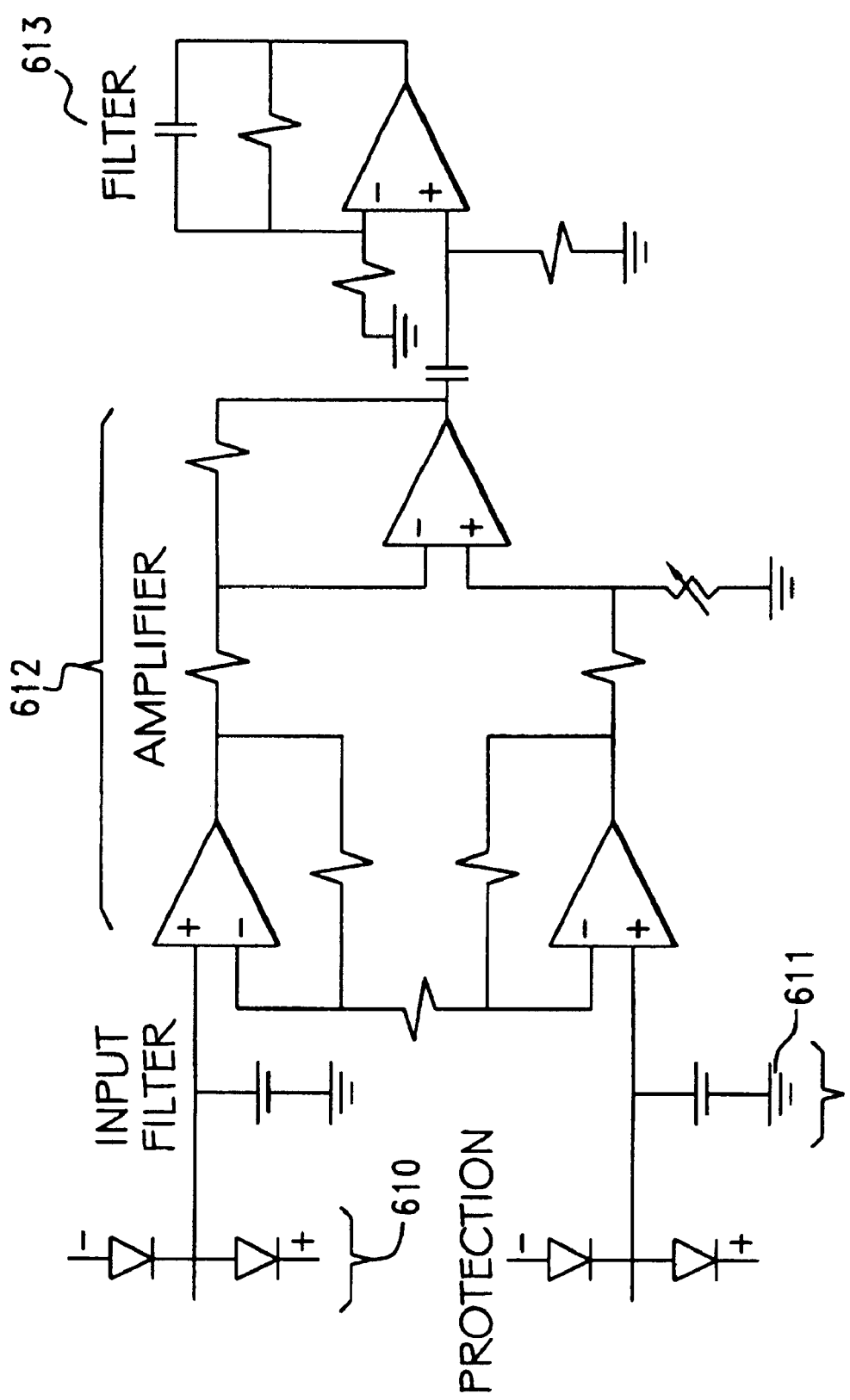

Preferably the implanted device consists of a casing or a can made of biocompatible and hermetically sealed case consistent with long term implantation in the hostile environment of the body (with its warm temperature, humidity, blood, etc.). The can is shaped in a variety of forms illustrated in FIG. 2 and FIG. 3. The circuitry associated with the sensor is housed inside this can and may be driven by battery power, typically one of the many contemporary pacemaker/defibrillator batteries using lithium or lithium ion or polymer battery technology well known in the art. The internal circuitry may utilize ultra-low power analog and digital circuit components built from miniaturized packages and running off the battery power supply. One overall schematic design is illustrated in FIG. 6(*a*) and consists of the input protection stage (601) which serves to protect the amplifier from possible shock hazards. This front-end should also meet electrical safety and leakage specifications conforming to safety standards as set by AAMI, American Heart Association and other standard setting bodies. This stage is followed by the amplifier (602) and followed by electrical isolation circuitry (603), if necessary. Isolation can be electrical or optical. The isolation circuit is followed by the output stage (604) which feeds all the analog signals from multiple channels into a multiplexer, MUX (605). The multiplexed signal is digitized using an A/D converter (analog to digital converter) (606) and then fed into a microprocessor (607). The principal circuit component is the EGM amplifier, which is designed using operational amplifiers as illustrated in FIG. 6(*b*). The amplifier circuitry consists of protection (610) and filtering (611) components (including diodes, capacitors and inductive chokes), operational amplifier based instrumentation amplifier (612), and active circuit filters for band-pass filtering (613). In various embodiments, the hardware implementation may use a low power, low voltage microprocessor or a custom-designed ASIC or a fully custom VLSI circuit. In an alternative embodiment, the hardware would be contained, or otherwise piggy-backed onto an implantable pacemaker or cardioverter-defibrillator. In this case the ischemia detection technology would use information derived from the existing leads of the implanted pacemaker or defibrillator. Also, the detection software would be embedded in the RAM or the ROM and executed by the microprocessor of the implanted pacemaker or cardioverter-defibrillator.

Figure 7A:
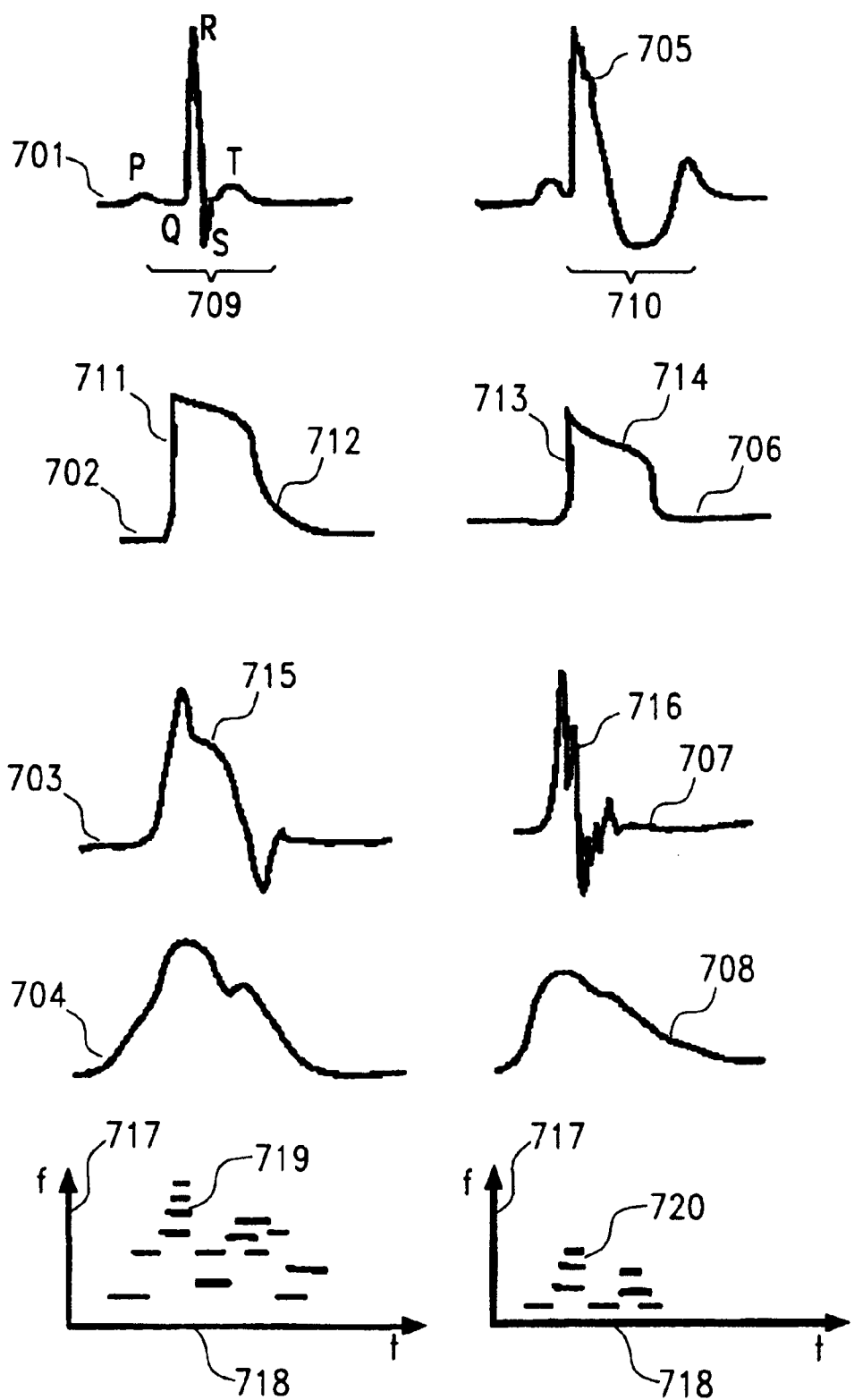
FIG. 7 illustrates (a) the depolarization and repolarization signals of the electrocardiogram, the action potential, normal and ischemic EGM, the pressure signals, and time-frequency response characteristics of the EGM; and (b & c) the electrical activation pattern on the heart as visualized by isochronal conduction distribution in (b) normally conducting zones and (c) ischemic zones.
Figure 7B:
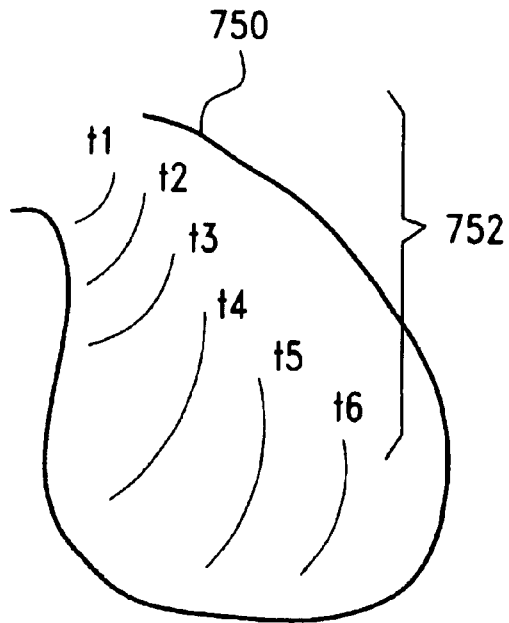
Figure 7C:
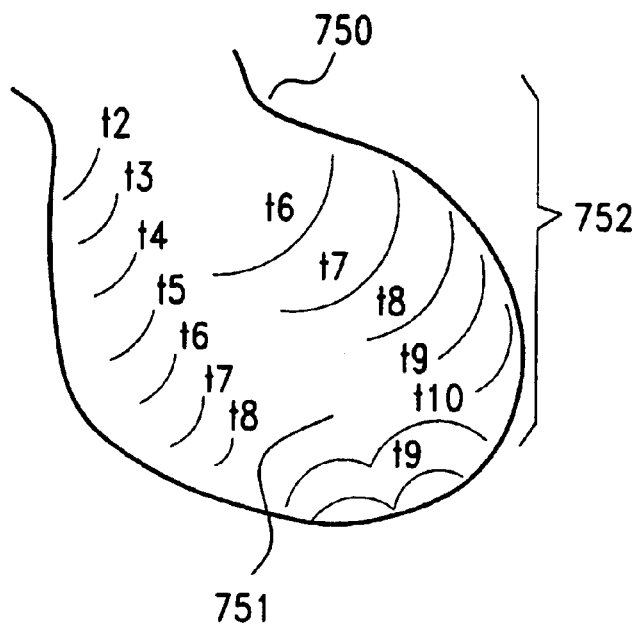

The sensors of the implanted device are preferably configured to capture the EGM signal and other physiologic data. From these signals and data, algorithms implemented by the microprocessor and its software identify the ischemic event. Embodiments utilize the EGM signals from inside the body using a plurality of sensors placed inside the thorax and in and around the heart. The sensors preferably seek to mimic the internal or implanted form of the Einthoven triangle and the 12 lead electrocardiographic system. The complete 12 lead system may not always be used and the MI/I event can be captured from only a limited set of leads and electrodes. The complete or partial set of these sensors, so arranged, provide a projected view of the heart's dipole at various sensor locations. The signals recorded from a sensor then give an indication of the MI/I event in its vicinity and the recorded pattern is indicative of the degree of severity of the MI/I event. Certain embodiments utilize both depolarization and repolarization signal components of the EGM signal to detect ischemia events. As illustrated in FIG. 7, ECG signal (701) is accompanied by the action potential signal (702), the EGM signal (703) and the pressure signal (704). Under MI/I conditions, these respective signals may be modified as shown in (705, 706, 707 and 708). Note the appearance of notches in the QRS complex and depression of the ST-segrnent (705 and 710). Correspondingly, the action potential (706) shows change in upstroke (713), duration and shape (714). Consequently, the EGM signal shows fractionation and multiple depolarization and changed shape (707). The ventricular pressure signal shows a reduction in magnitude as well as shape change (708). The ischemic conditions are some times localized to parts of the heart (focal ischemia or infarct) and at other times throughout the heart (global). Ischemia results in slowed conduction and possible fractionation of the conduction patterns. FIGS. 7(b) and 7(c) illustrate the conduction on the heart (750), with FIG. 7(b) illustrating the conduction in normal conditions (left), with traces (752) showing isochronal lines t1 through t6 (places receiving simultaneous activation). An infarcted is indicated as a region 751 on the heart with no isochronal lines, and consequently it is a region which alters the conduction pattern. Therefore, under ischemic conditions, as illustrated in FIG. 7(c), the conduction pattern (752) is altered as indicated by the isochrones t1 through t10. The isochrones show different pathways, indicating dispersion and fractionation of conduction. This dispersion and fractionation of conduction produces the EGM signal depicted for ischemic hearts (707) and its features thereof (716).

The EGM signal for normal versus ischemic myocardial tissue can be distinguished using a variety of means including waveform analysis done in both the temporal and frequency domain and combination of both, which is called a time-frequency method. FIG. 7(a) graphically illustrates the EGM signal for a healthy heart (703) with a relatively large major peak and related inflection and transition points corresponding to depolarization and repolarization events occurring during the cardiac cycle (702). In contrast, the ischemic signal shown in (707) shows significantly more peaks and has unusual transitional points (716). This phenomenon is known as fragmentation and is readily distinguishable. An alternate approach is to detect ischemia in the frequency domain. FIGS. 7 also illustrates the time-frequency analysis of the EGM signal. The EGM signal is analyzed through Fourier analysis which is well known in the art and its frequency components are thus obtained. Since the EGM signal is time-varying, time-frequency analysis is more suitable so as to obtain instantaneous frequencies at different times in the cardiac cycle. Magnitude of signal power, indicated by horizontal lines at various frequencies (717) and plotted versus time (718) is calculated. In this case, the ischemic EGM time-frequency distribution (719) is distinguished from the time-frequency distribution of the healthy EGM waveform (720) by a broader range of frequencies at one or more depolarization, repolarization and fractionation event locations. Further during repolarization, there is shift towards lower frequencies corresponding to the ST-segment elevation or depression and T-wave morphology changes in the ECG. Several different approaches of time-frequency and time-scale analyses are applicable to calculating localized frequency information at various instants of the EGM signals. Normal and ischemic EGM waveforms/signals are thus distinguished and the electrodes or sensors displaying the characteristic changes identify ischemia in their vicinity. This approach is extended to analysis of signals from various sensors. FIG. 7(a) shows the cavitary pressure signal in normal (704) and ischemic (707) hearts. Analogously, a cavitary probe measuring conductance can obtain an estimate of the ventricular volume by methods well known in the art. The magnitude and morphology of the conductance signal is also indicative of MI/I. Analogously, ventricular volume signal assessed by the aforementioned conductance method also identifies local changes in the conductance and proportionately the volume in the region of the ventricular cavity. Therefore, a comparison of such signals placed in different positions in the heart (e.g. 505, 508, 509), allows estimation of ventricular volumes at different points in the cardiac cycle and at different locations in heart. Information from the EGM signals (electrical conduction) and hemodynamic /mechanical signals (conductance, pressure, ventricular volume, blood volume, velocity etc.), may be used separately or combined by one or more algorithms, programmable devices or modified pacemaker, cardioverter, defibrillator systems seeking to detect an ischemic event. Ischemic diagnostic fiction may be further enhanced by combining analysis of ECG and hemodymanic data with metabolic/chemical data (e.g. PO2, CO2, pH, CK (creatine kinase)) collected using in dwelling sensors which may be chemical FETs, optical fibers or otherwise polarimetric or optical based, and the like, all well known in the art.

In another embodiment of the ischemia detection sensors, a use is made of the multiple sensors spanning the lead in the ventricular cavity. The sensors (505 or 508 or 509) in FIG. 5 capture the changes in the EGM signals in their vicinity. An analysis of the relative morphologies would help identify the ischemia in the vicinity of the electrode. The electrode sensors record the EGM signals whose morphology or frequency characteristics in normal or MI/I conditions is similarly analyzed by the methods illustrated in FIG. 7(a). The EGM signal recorded and analyzed results from spontaneous heart beats or from paced beats. Spontaneous heart beats are produced by the heart's own natural rhythm. Paced beats are produced by a pacing electrode usually at the tip of the lead placed in the atrial or the ventricular cavity. The morphology and the frequency characteristics of the paced beats are analyzed for MI/I condition.

Figure 8A:
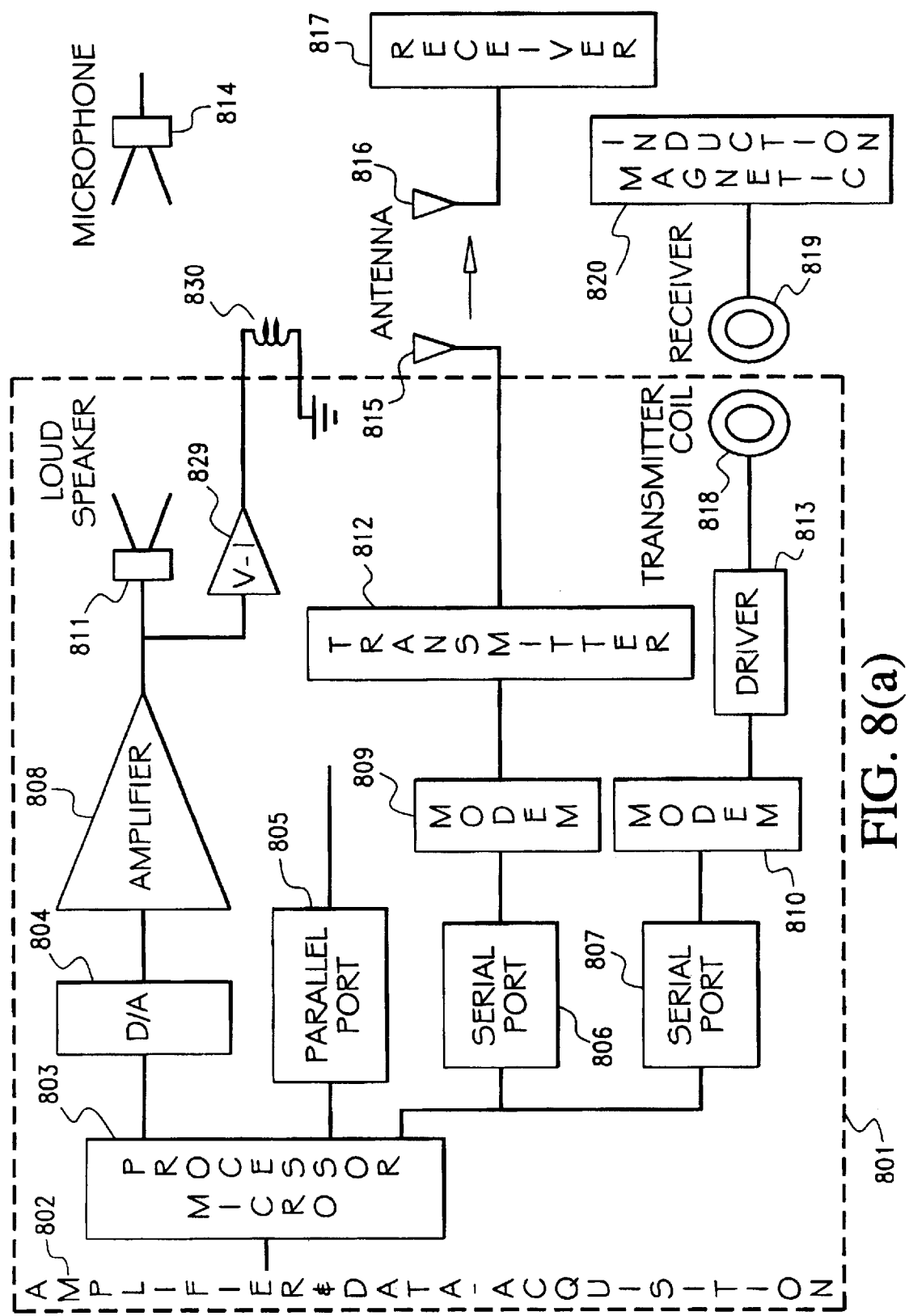
FIG. 8(*a*) illustrates various communication links between the implantable device and the external monitoring devices, including alerting the subject with the aide of a loud speaker, vibrator or electrical stimulation, communication to and external device via RF communication, audio communication, and magnetic field modulation according to embodiments of the present invention.

Once an incident of MI/I is detected, the patient or the medical care giver needs to be informed so that quick intervention may be taken. Noting that certain aspects of embodiments relate to an implanted device, the device needs to communicate the signal out to the patient and/or the physician. FIG. 1 provided a scheme for the communication between the implanted device (101) and the subject (103) or the external device (108). Now, for further detail, FIG. 8 illustrates an implanted device (801) comprising its amplifier and data-acquisition system (802) and microprocessor (803) communicates data and message to the subject or the external device via a D/A converter (804), a parallel port (805), a serial port (806 or 807). The D/A converter is connected to an amplifier (808) which drives a loud speaker, buzzer or a vibrator (811). The external device may receive this information via a microphone (815). The subject may preferably receive the alert message via audio or vibratory signal (811). Alternately, the subject may receive the indication of an MI/I via an electrical stimulus feedback delivered via a voltage to current converter, V-I (829) delivered to the case of the implanted device or to a stimulating lead. The serial port communicates the electrical signals via a modem (809), and a transmitter (812) to an antenna (815) for radio frequency or audio telemetry to the external device. The external device receives the radio telemetry communication via an antenna (816) and a receiver (817) and subsequently conveys these data to a computer connected to the receiver. Alternately, the implanted device may use a serial port (807), connected to a modem (810) and a transmitting coil capable of generating and receiving magnetic fields (818). By pulsed or alternating magnetic field, a message pertaining to the MI/I event or digitized data from the microprocessor (803) are relayed to the external device. An external coil capable of generating or receiving magnetic field communicates the message to and from the implanted device (819) via magnetic induction. The magnetic field fluctuations are processed and a message or data stream may be communicated to a computer connected to the external device. These are among many alternative means to enable communication between the implanted device and the external device may be operated/worn by the physician or the patient. Other communication technologies well known in the art may also be utilized. The implanted and the external device engage in a unidirectional (sending the MI/I alert or sending actual digital or analog data over the link) or bidirectional (external device sending commands, internal sending the data, for example).

Figure 8B:
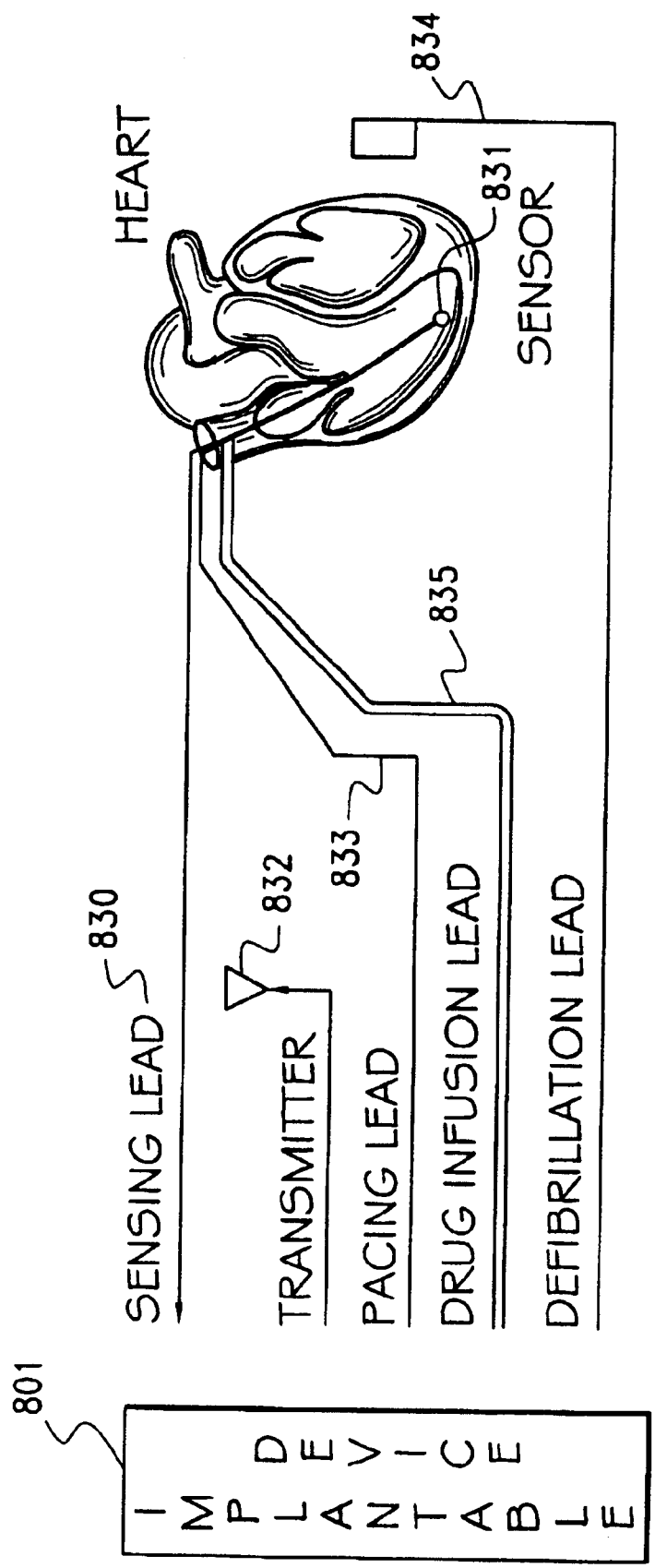

Certain embodiments also include devices and methods for taking a therapeutic action. The therapeutic action is possible because implanted device provides an early indication of an event of MI/I. Therefore, there may be adequate time for this system to perform therapeutic actions to prevent or minimize the development of an infarction. In various embodiments of the invention, therapeutic actions may comprise: infusion of thrombolytic agents such as TPA and streptokinase or anticoagulant agents such as heparin. Since it is known that there is treatment window of several hours after infarction which can prevent more serious medical complications, a timely bolus or steady release of these medicines may prevent or otherwise ameliorate the conditions that may be precipitating the MI/I. FIG. 8(b) illustrates the schema in which the implanted device (801) equipped with a lead (833) connected to a sensing means (831) initiates the action of transmitting a message via a transmitter (832) in a manner described previously. It also initiates infusion of any of the aforementioned drugs via an infusion line or a catheter (835). For example, the drug may be in the catheter tip itself embedded in a slow release polymeric matrix whose release is actuated by the implanted device. Alternately, the drug may be in the device itself and released via infusion tubing (835). The acute MI/I may precipitate a life-threatening arrhythmia. In case such an event, involving arrhythmias such as ventricular tachycardia or fibrillation, the implanted device may initiate electrical rescue therapy, such as pacing, cardioversion or defibrillation. An electrical shock may be given via two leads, which may be a combination of the can of the implanted device (801) and an intracavitary lead (833) or a combination of subcutaneous or an epicardial or intrathoracic lead (834) and an intracavitary lead. Thus, the implanted device would initiate the therapeutic procedures semi-automatically by first alerting the patient or automatically via infusion of a drug or delivery of electrical rescue shock.

While aspects of the present invention have been described with reference to the aforementioned applications, this description of various embodiments and methods shall not be construed in a limiting sense. The aforementioned is presented for purposes of illustration and description. It shall be understood that all aspects of the invention are not limited to the specific depictions, configurations or relative proportions set forth herein which may depend upon a variety of conditions and variables. The specification is not intended to be exhaustive or to limit the invention to the precise forms disclosed herein. Various modifications and changes in form and detail of the particular embodiments of the disclosed invention, as well as other variations of the invention, will be apparent to a person skilled in the art upon reference to the present disclosure. For example, the logic to perform various analyses as discussed above and recited in the claims may be implemented using a variety of techniques and devices, including software under microprocessor control or embedded in microcode, or implemented using hard wired logic.

While the invention described above presents some of the preferred embodiments, it is to be understood that the invention in not limited to the disclosed embodiment but rather covers various modifications and equivalent arrangements included within the spirit and scope of the appended claims.

What is claimed is:

1. A method comprising:
   monitoring the heart for evidence of myocardial ischemia/infarction (MI/I) using a device implanted into a subject, the device including at least one lead positioned at least partially in at least one of the heart and the vascular system; and
   alerting the subject upon detection of MI/I using a signal generated by the implanted device.

2. A method as in claim 1, wherein the detecting MI/I comprises:
   sensing an electrogram signal; and
   determining the occurrence of MI/I based on the electrogram signal.

3. A method as in claim 1, wherein the detecting MI/I comprises:
   positioning a plurality of leads and sensors in the subject;
   transmitting data from the sensors to a microprocessor; and
   determining whether an MI/I event has occurred.

4. A method as in claim 3, wherein the alerting the subject comprises sending the signal to a device external of the subject.

5. A method as in claim 1, further comprising sending a signal to a device external of the subject.

6. A method as in claim 1, further comprising initiating therapy within the subject after detecting MI/I.

7. A method as in claim 1, further comprising providing a supply of a medicine as part of the device implanted into the subject and supplying a dose of the medicine to the subject after detecting MI/I.

8. A method for monitoring the heart of a subject for MI/I inside of the subject, comprising:

implanting into a subject's chest a container including circuitry and a microprocessor;

providing a plurality of sensors electrically connected to the circuitry;

positioning at least one sensor in the subject's cardiovascular system; and determining whether MI/I has occurred.

9. A method as in claim 8, wherein the plurality of sensors includes at least one sensor from a group consisting of electrical, mechanical and hemodynamic sensors.

10. A method as in claim 9, wherein the microprocessor includes at least one algorithm for interpreting a signal generated by the at least one sensor and determining whether MI/I has occurred.

11. A method as in claim 9, wherein the container is implanted subcutaneaously.

12. A method as in claim 9, wherein the container is implanted with intracavitory connections.

13. A method as in claim 9, wherein the container is implanted with epicardial connections.

14. A method as in claim 9, wherein the container is implanted with electrical access to a plurality of chambers of the heart.

15. A method for monitoring the heart of a subject for MI/I inside of the subject. comprising:

implanting into a subject's chest a container including circuitry and a microprocessor;

providing a plurality of sensors electrically connected to the circuitry;

positioning at least one sensor in or on the heart of the subject; and determining whether MI/I has occurred;

wherein the plurality of sensors includes at least one sensor from a group consisting of electrical, mechanical and hemodynamic sensors; and wherein the container is fully implanted within the blood vessels and cavity of the heart.

16. A method for monitoring the heart of a subject for MI/I inside of the subject, comprising:

implanting into a subject's chest a container including circuitry and a microprocessor;

providing a plurality of sensors electrically connected to the circuitry;

positioning at least one sensor in or on the heart of the subject; and determining whether MI/I has occurred;

wherein the plurality of sensors includes at least one sensor from a group consisting of electrical, mechanical and hemodynamic sensors; and wherein the container is implanted with access to intracavitary blood.

17. A method for monitoring the heart of a subject for MI/I inside of the subject, comprising:

implanting into a subject's chest a container including circuitry and a microprocessor;

providing a plurality of sensors electrically connected to the circuitry;

positioning at least one sensor in or on the heart of the subject; and determining whether MI/I has occurred;

wherein the plurality of sensors includes at least one sensor from a group consisting of electrical, mechanical and hemodynamic sensors; and wherein the container is implanted with access to intravascular blood.

18. A method as in claim 8, wherein at least one sensor is mounted on the container.

19. A method as in claim 8, wherein the sensors are attached to leads extending from the container, the method further comprising positioning leads at three orthogonal locations on the container.

20. A method as in claim 8, wherein the sensors are positioned in a configuration selected from the group consisting of orthogonal, Einthoven triangle, and chest lead configuration.

21. A method comprising:

monitoring the heart for evidence of myocardial ischemia/infarction (MI/I) using a device implanted into a subject;

alerting the subject upon detection of MI/I using a signal generated by the implanted device;

wherein the detection of MI/I comprises positioning a plurality of leads and sensors in the subject, transmitting data from the sensors to a microprocessor, and determining whether an MI/I event has occurred; and wherein the positioning a plurality of leads comprises positioning the leads in an internal Einthoven triangle placement.

22. A method as in claim 3, wherein the positioning a plurality of leads comprises positioning the leads so that the sensors are configured in an orthogonal pattern.

23. A method as in claim 3, wherein the positioning a plurality of leads comprises placing the leads to form sensing configurations in a plurality of regions in the heart that enhance sensitivity to MI/I.

24. A method for monitoring a heart in a subject for evidence of MI/I comprising:

implanting a container including circuitry and a microprocessor in the subject; and providing a plurality of leads extending from the container, wherein at least one lead extends to a position inside of the heart.

25. A method as in claim 24, further comprising positioning a plurality of leads in a plurality of heart chambers.

26. A method as in claim 24, further comprising positioning a plurality of leads to provide electrical access to a plurality of chambers of the heart.

27. A method as in claim 24, further comprising positioning routing at least one lead inside a heart cavity selected from the group consisting of the atrial and the ventricular.

28. A method as in claim 24, further comprising positioning at least one lead to provide electrical access to epicardial regions of the heart.

29. A method as in claim 24, further comprising positioning at least one lead to provide electrical access to thoracic regions surrounding the heart.

30. A method as in claim 24, further comprising positioning at least one lead to provide electrical access to subcutaneous regions adjacent in the vicinity of the heart.

31. A method as in claim 24, further comprising positioning multiple electrically conductive sensor elements on at leaf one lead.

32. A method as in claim 24, further comprising positioning multiple sensor elements selected from the group consisting of unipolar elements and bipolar elements on at least one lead.

33. A method as in claim 24, further comprising mounting at least one sensor element on the container.

34. A method as in claim 24, further comprising:

transmitting at least one signal through at least one of the leads to the circuitry;
amplifying the signal;
filtering the signal; and
converting the signal from an analog signal to a digital signal.

35. A method as in claim 34, wherein a plurality of signals are transmitted through a plurality of leads and are delivered to the circuitry, further comprising feeding the signals to a multiplexer, converting the signal from an analog signal to a digital signal, and delivering the signal to the microprocessor.

36. A method comprising:
monitoring the heart for evidence of myocardial ischemia/infarction (MI/I) using a device implanted into a subject; and
alerting the subject upon detection of MI/I using a signal generated by the implanted device;
wherein the detecting myocardial ischemia comprises using at least one sensor selected from the group consisting of a cavitary pressure sensor, a myocardial cavitary volume sensor, a blood pO2 sensor, a blood pH sensor, a blood lactate sensor, and a tissue impedance sensor;
wherein the sensor comprises a portion of the device implanted into the subject; and
wherein the sensor is capable of distinguishing a myocardial ischemia condition from a non-myocardial ischemia condition.

37. A method as in claim 36, wherein at least one sensor comprises a myocardial cavitary volume sensor that operates using conductance.

38. A method as in claim 1, wherein the detecting myocardial ischemia includes separating a normal from an ischemic-electrogram signal, the method comprising analyzing the electrogram signal using an analysis selected from the group consisting of (1) an electrogram waveform analysis for temporal features, (2) an electrogram waveform analysis using time-domain signal analysis methods, (3) an electrogram waveform analysis using a frequency domain method such as FFT and filtering, and (4) an electrogram waveform analysis using a combined time and frequency analysis method.

39. A method as in claim 38, wherein the analyzing the electrogram signal comprises using an electrogram waveform analysis for at least one temporal feature selected from the group consisting of peaks and inflections.

40. A method comprising:
monitoring the heart for evidence of myocardial ischemia/infarction (MI/I) using a device implanted into a subject; and
alerting the subject upon detection of MI/I using a signal generated by the implanted device;
wherein the detection of myocardial ischemia includes separating a normal from an ischemic electrogram signal, and includes analyzing the electrogram signal using a frequency domain method selected from the group consisting of fast Fourier transform and filtering.

41. A method comprising:
monitoring the heart for evidence of myocardial ischemia/infarction (MI/I) using a device implanted into a subject; and
alerting the subject upon detection of MI/I using a signal generated by the implanted device;
wherein the detection of myocardial ischemia includes separating a normal from an ischemic electrogram signal, and includes analyzing the electrogram signal using a combined time and frequency analysis selected from the group consisting of joint time frequency distributions and wavelet analysis.

42. A method comprising:
monitoring the heart for evidence of myocardial ischemia/infarction (MI/I) using a device implanted into a subject; and
alerting the subject upon detection of MI/I using a signal generated by the implanted device, wherein the implanting device directly alerts the subject using a signal selected from the group consisting of an electrical signal, a magnetic signal, an electromagnetic signal, and an auditory signal.

43. A method as in claim 1, wherein the device comprises a portion of an implanted apparatus selected from the group consisting of a pacemaker, a cardioverter, a defibrillator, a cardiac assist device, and an infusion pump.

44. A method as in claim 24, further comprising a plurality of sensors coupled to the plurality of leads, and detecting the location of a MI/I site by sensing signals from sensors located at different position within the subject and analyzing the changes in the signal at the different positions.

45. A method as in claim 44, wherein the analyzing comprises calculation of cardiac dipoles of the MI/I site by dipole projection.

46. A method as in claim 44, wherein a plurality of the leads are positioned orthogonal to each other.

47. A method as in claim 44, wherein the detecting the location is determined using leads selected from the group consisting of orthogonal leads, Einthoven triangle leads, chest leads, and endocardial cavita leads.

48. A method comprising:
monitoring the heart for evidence of myocardial ischemia/infarction (MI/I) using a device implanted into a subject; and
alerting the subject upon detection of MI/I using a signal generated by the implanted device, wherein the alerting the subject is carried out by electrical stimulation of the subject.

49. A method comprising:
monitoring the heart for evidence of myocardial ischemia/infarction (MI/I) using a device implanted into a subject; and
alerting the subject upon detection of MI/I using a signal generated by the implanted device, wherein the alerting the subject is carried out by a communication generated by the implanted device, the communication selected from the group consisting of auditory communication and vibratory communication.

50. A method as in claim 1, wherein the alerting the subject is carried out using an electromagnetic link to an external device worn by the subject.

51. A method as in claim 1, wherein alerting the subject is carried out by activating a device selected from the group consisting of an external pager and external alarm.

52. A method as in claim 1, further comprising alerting a person other than the subject upon detection of a MI/I a method selected from the group consisting of electrical communication via RF links, modulation of a magnetic field signal, electromagnetic transmission, auditory transmission, digital encoding and transmission of a signal, and analog modulation and transmission of a signal.

53. A method as in claim 8, further comprising communicating between the implanted container and a device external to the subject, comprising positioning the external device adjacent to the torso of the subject.

54. A method as in claim 8, further comprising communicating between the implanted container and a device external to the subject.

55. A method for monitoring the heart of a subject for MI/I inside of the subject, comprising:
- implanting into a subject's chest a container including circuitry and a microprocessor;
- providing a plurality of sensors electrically connected to the circuitry;
- positioning at least one sensor in or on the heart of the subject;
- determining whether MI/I has occurred; and
- communicating between the implanted container and a device external to the subject;
- wherein a modem protocol is used to communicate between the implanted container and a telephone.

56. A method as in claim 8, further comprising communicating between the implanted container and a device external to the subject, wherein the communicating is carried out using radiotelemetry.

57. A method as in claim 8, further comprising communicating between the implanted container and a device external to the subject, wherein the communicating is carried out using links between the implanted container and a computer system.

58. A method for monitoring the heart of a subject for MI/I inside of the subject, comprising:
- implanting into a subject's chest a container including circuitry and a microprocessor;
- providing a plurality of sensors electrically connected to the circuitry;
- positioning at least one sensor in or on the heart of the subject;
- determining whether MI/I has occurred; and
- comprising communicating between the implanted container and a device external to the subject, wherein the communicating is carried out using links between the implanted container and a health care provider's computer system.

59. A method as in claim 54, wherein the device external to the subject comprises a device selected from the group consisting of a telephone and a pager.

60. A method for monitoring the heart of a subject for MI/I inside of the subject, comprising:
- implanting into a subject's chest a container including circuitry and a microprocessor;
- providing a plurality of sensors electrically connected to the circuitry;
- positioning at least one sensor in or on the heart of the subject;
- determining whether MI/I has occurred; and
- communicating between the implanted container and a device external to the subject, wherein the device external to the subject includes an emergency care network.

61. A method of manufacturing an implantable device elected from the group consisting of pacemakers, cardio-defibrillators, atrial defibrillators, ventrical defibrillators, cardiac assist devices, and drug infusion devices, the method including incorporating into the implantable device circuitry for monitoring the occurrence of a MI/I in a subject and providing a signal indicating the occurrence of a MI/I, the method further including incorporating into the implantable device at least one lead adapted to extend into the subject's vascular system.

62. A method as in claim 61, further comprising delivering the signal to a device external to the implantable device.

63. A method as in claim 61, further comprising alerting the subject of the occurrence of a MI/I.

64. An apparatus for detecting MI/I in a subject, comprising:
- an implantable container;
- at least one lead adapted for insertion into the heart;
- at least one sensor adapted for insertion into the heart; and
- a microprocessor in the container to analyze data from the at least one sensor.

65. An apparatus as in claim 64, further comprising circuitry to transmit a signal from the sensor to the microprocessor.

66. An apparatus as in claim 65, further comprising means to alert the subject after detecting MI/I.

67. An apparatus as in claim 65, further comprising means to communicate with at least one device external to the subject.

68. An apparatus as in claim 64, further comprising means for initiating therapy after detecting MI/I.

69. An apparatus as in claim 65, further comprising a supply of at least one drug adapted for insertion into the body, wherein the supply is released upon receiving a signal from the microprocessor.

70. An apparatus as in claim 64, wherein the container comprises a can that is adapted to fit inside of the subject's heart.

71. An apparatus as in claim 64, wherein the container comprises a can comprising the shape of an implanted device selected from the group consisting of a pacemaker, a cardioverter, a defibrillator, a cardiac assist device, and an infusion pump.

72. An apparatus as in claim 64, wherein the container comprises a can having a triangular shape.

73. An apparatus as in claim 64, wherein the container comprises a can shaped in the form of a pouch adapted to surround a portion of a heart.

74. An apparatus as in claim 64, wherein the container comprises a can shaped to include three orthogonal locations for mounting electrodes.

75. An apparatus as in claim 64, wherein the container comprises a can shaped to include locations to permit Einthoven triangle electrode placement.

76. An apparatus as in claim 64, wherein the container comprises a can, wherein at least one sensor is mounted on the can.

77. An apparatus as in claim 64, further comprising an electrode, wherein the sensor is attached to the lead through the electrode.

78. An apparatus as in claim 64, wherein the sensor includes an electrode coupled to the lead.

79. An apparatus as in claim 78, comprising a plurality of electrodes adapted for insertion into the heart in a variety of locations.

80. An apparatus as in claim 64, wherein the lead is configured to transmit electrogram signals from at least two locations selected from the group consisting of atrial heart cavity locations, ventricular heart cavity locations, epicardial heart locations, thoracic locations surrounding a heart, and subcutaneous locations adjacent to a heart.

81. An apparatus as in claim 64, wherein at least one lead includes a plurality of sensors coupled thereto.

82. An apparatus as in claim 64, wherein at least one lead includes a plurality of electrically conductive sensor elements thereon.

83. An apparatus as in claim 64, wherein at least one lead includes multiple unipolar elements.

84. An apparatus as in claim 64, wherein at least one lead includes multiple bipolar elements.

85. An apparatus as in claim 64, wherein the container acts as a reference for electrical common.

86. An apparatus as in claim 64, wherein at least one sensor is mounted on the container and at least one sensor is mounted to a lead a distance away from the container.

87. An implantable apparatus for monitoring a subject for MI/I comprising:
a hermetically sealed container;
circuitry disposed within the container;
an analog to digital converter disposed within the container;
a logic device disposed within the container; and
a feed-through interface between at least one lead extending from the container and the circuitry.

88. An apparatus as in claim 87, wherein the logic device comprises a microprocessor.

89. An apparatus as in claim 87, further comprising at least one amplifier disposed within the container.

90. An apparatus as in claim 87, further comprising at least one filter disposed within the container.

91. An apparatus as in claim 87, further comprising at least one sensor to recognize a MI/I condition, the sensor being coupled to a lead.

92. An apparatus as in claim 91, wherein the sensor comprises a sensor selected from the group consisting of a blood pO2 sensor, a blood pH sensor, a blood lactate sensor, a blood temperature sensor, and a tissue impedance sensor.

93. An apparatus as in claim 87, wherein the monitoring for MI/I includes separating normal from ischemic electrogram signals by means to perform electrogram waveform analysis for temporal features including peaks and inflections.

94. An apparatus as in claim 87, wherein the monitoring for MI/I includes separating normal from ischemic electrogram signals by means to perform electrogram waveform analysis using time-domain signal analysis.

95. An apparatus as in claim 87, wherein the monitoring for MI/I includes separating normal from ischemic electrogram signals by means to perform electrogram waveform analysis using frequency domain methods.

96. An apparatus as in claim 87, wherein the monitoring for MI/I includes separating normal from ischemic electrogram signals by means to perform electrogram waveform analysis using combined time and frequency analysis.

97. An apparatus as in claim 87, wherein the monitoring for MI/I includes separating normal from ischemic electrogram signals by means to analyze changes in depolarization and repolarization.

98. An apparatus as in claim 87, wherein the monitoring for MI/I includes means for detecting a MI/I signal by determining its temporal features synchronous to the Q, R, S, and T waves in an electrogram signal.

99. An apparatus for detecting MI/I in a subject, comprising:
means for detecting MI/I; and
means for generating a signal to alert the subject about the MI/I;
wherein the means for detecting and the means for generating the signal are adapted to be implantable into at least one of the heart and vascular system in the subject.

100. An apparatus for detecting MI/I in a subject, comprising:
an implantable container;
at least one lead adapted for insertion into the heart and electrically connected to circuitry in the container;
at least one sensor coupled to the at least one lead and adapted for insertion into the heart;
a microprocessor in the container to analyze data from the at least one sensor; and
a transmitter.

101. An apparatus as in claim 100, wherein the transmitter comprises a device selected from the group consisting of an RF transmitter, an electrical transmitter, and an electromagnetic transmitter.

102. An apparatus as in claim 100, wherein the transmitter comprises means to transmit a signal to the subject.

103. An apparatus as in claim 102, wherein the transmitter comprises means to transmit a signal to a device external from the subject.

104. An apparatus as in claim 100, wherein the implantable container is adapted to fit within a heart cavity.

105. An apparatus as in claim 100, wherein the implantable container is adapted to fit transvenously within a subject.

106. A method as in claim 3, wherein the positioning a plurality of leads comprises positioning the leads in an internal Einthoven triangle placement.

107. A method as in claim 1, wherein the detecting myocardial ischemia comprises:
using at least one sensor selected from the group consisting of a cavitary pressure sensor, a myocardial cavitary volume sensor, a blood pO2 sensor, a blood pH sensor, a blood lactate sensor, and a tissue impedance sensor;
wherein the sensor comprises a portion of the device implanted into the subject; and
wherein the sensor is capable of distinguishing a myocardial ischemia condition from a non-myocardial ischemia condition.

108. A method as in claim 38, wherein the analyzing the electrogram signal comprises using a frequency domain method selected from the group consisting of fast Fourier transform and filtering.

109. A method as in claim 38, wherein the analyzing the electrogram signal comprises using a combined time and frequency analysis selected from the group consisting of joint time frequency distributions and wavelet analysis.

110. A method as in claim 1, wherein the alerting signal comprises a signal selected from the group consisting of an electrical signal, a magnetic signal, an electromagnetic signal, and an auditory signal.

111. A method as in claim 1, wherein the alerting the subject is carried out by electrical stimulation of the subject.

112. A method as in claim 1, wherein the alerting the subject is carried out by a communication selected from the group consisting of auditory communication and vibratory communication.

113. A method as in claim 9, wherein the container is fully implanted within the blood vessels and cavity of the heart.

114. A method as in claim 9, wherein the container is implanted with access to intracavitary blood.

115. A method as in claim 9, wherein the container is implanted with access to intravascular blood.

116. A method as in claim 54, wherein a modem protocol is used to communicate between the implanted container and a telephone.

117. A method as in claim 8, further comprising communicating between the implanted container and a device external to the subject, wherein the communicating is carried out using links between the implanted container and a health care provider's computer system.

118. A method as in claim 8, further comprising communicating between the implanted container and a device external to the subject, wherein the device external to the subject includes an emergency care network.

119. A method as in claim 61, wherein the at least one lead is adapted to extend into the subject's heart.

120. A method as in claim 87, wherein at least one lead extending from the container is adapted to be positioned in the subject's heart.

121. A method as in claim 87, wherein at least one lead extending from the container is adapted to be positioned in the subject's vascular system.

122. A method as in claim 87, wherein the container is positioned within the subject's cardiovascular system.

* * * * *